(12) United States Patent
Leutenegger et al.

(10) Patent No.: US 10,174,373 B2
(45) Date of Patent: Jan. 8, 2019

(54) NUCLEIC ACID AMPLIFICATION CONTROLS AND KITS AND METHODS OF USE THEREOF

(71) Applicant: IDEXX Laboratories, Inc., Westbrook, ME (US)

(72) Inventors: Christian Leutenegger, Dixon, CA (US); Michael John Angelichio, Kennebunk, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 594 days.

(21) Appl. No.: 14/436,739

(22) PCT Filed: Oct. 18, 2013

(86) PCT No.: PCT/US2013/065681
§ 371 (c)(1),
(2) Date: Apr. 17, 2015

(87) PCT Pub. No.: WO2014/063051
PCT Pub. Date: Apr. 24, 2014

(65) Prior Publication Data
US 2015/0275294 A1 Oct. 1, 2015

Related U.S. Application Data

(60) Provisional application No. 61/715,596, filed on Oct. 18, 2012, provisional application No. 61/790,854, filed on Mar. 15, 2013.

(51) Int. Cl.
C12Q 1/68 (2018.01)
C12Q 1/6876 (2018.01)
C12Q 1/6844 (2018.01)
C12Q 1/686 (2018.01)

(52) U.S. Cl.
CPC ........... *C12Q 1/6876* (2013.01); *C12Q 1/686* (2013.01); *C12Q 1/6844* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 5,418,149 A | 5/1995 | Gelfand et al. | |
| 5,455,170 A | 10/1995 | Abramson et al. | |
| 5,654,143 A | 8/1997 | Mallet et al. | |
| 5,674,738 A | 10/1997 | Abramson et al. | |
| 5,736,333 A | 4/1998 | Livak et al. | |
| 5,928,907 A | 7/1999 | Woudenberg et al. | |
| 5,952,202 A | 9/1999 | Aoyagi et al. | |
| 7,687,247 B1 | 3/2010 | Hartley et al. | |
| 7,883,871 B2 | 2/2011 | Lee et al. | |
| 7,981,606 B2 | 7/2011 | Emrich et al. | |
| 2004/0023207 A1* | 2/2004 | Polansky | A61K 31/00 435/5 |
| 2004/0072242 A1* | 4/2004 | Hunter | C12Q 1/689 435/7.1 |
| 2006/0134615 A1 | 6/2006 | Linder et al. | |
| 2007/0072212 A1* | 3/2007 | Vinayagamoorthy | C12Q 1/686 435/6.18 |
| 2009/0312393 A1* | 12/2009 | Poulain | C12N 15/111 514/44 A |
| 2010/0273143 A1 | 10/2010 | Brewer et al. | |
| 2012/0115154 A1 | 5/2012 | Hampikian | |

FOREIGN PATENT DOCUMENTS

| | | |
|---|---|---|
| EP | 1319716 | 6/2003 |
| WO | 1998/58083 | 12/1998 |
| WO | 02/33128 A2 | 4/2002 |
| WO | 2003/083051 | 10/2003 |
| WO | 2004/104229 | 12/2004 |
| WO | 2005/040396 | 5/2005 |

OTHER PUBLICATIONS

TaqMan® One-Step RT-PCR Master Mix Reagents Kit manual from Applied Biosystems (Year: 2010).*
Assays-on-Demand™ Gene Expression Products product insert from Applied Biosystems (Year: 2002).*
Heine et al. Rapid Detection of Highly Pathogenic Avian Influenza H5N1 Virus by TaqMan Reverse Transcriptase-Polymerase Chain Reaction. Avian Diseases 51:370-372. (Year: 2007).*
Osman et al. Real-time RT-PCR (TaqMan®) assays for the detection of Grapevine Leafroll associated viruses 1-5 and 9. Journal of Virological Methods 141:22-29. (Year: 2007).*
AgPath-ID™ One-Step RT-PCR Kit protocol from Applied Biosystems (Year: 2009).*
TaqMan® Ribosomal RNA Control Reagents protocol from Applied Biosystems (Year: 2002).*
Das et al., "Development of an Internal Positive Control for Rapid Diagnosis of Avian Influenza Virus Infections by Real-Time Reverse Transcription-PCR with Lyophilize Reagents", Journal of Clinical Microbiology, 44(9):3065-3073 (2006).
DeFoort et al., "Simultaneous Detection of Multiplex-Amplified Human Immunodeficiency Virus Type 1 RNA, Hepatitis C Virus RNA, and Hepatitis B Virus DNA Using a Flow Cytometer Microsphere-Based Hybridization Assay", J. Clin. Microbiol., 38(3):1066 (2000).
Fast-Track Diagnostics, "FTD respiratory pathogens", www.fast-trackdiagnostics.com/pages/order_cat, downloaded Jan. 8, 2013.

(Continued)

*Primary Examiner* — Samuel C Woolwine
(74) *Attorney, Agent, or Firm* — McDonnell Boehnen Hulbert & Berghoff LLP

(57) ABSTRACT

The invention provides components and methods for polymerase chain reaction assays. The assays minimize both handling of material and time spent running samples. For example, a single internal positive control (SPC) polynucleotide pair can provide a means to ensure proper nucleic acid purification for both RNA and DNA test targets. Additionally, standard cycling conditions for all diagnostic tests allow the user to run both RNA and DNA targets side-by-side.

15 Claims, 8 Drawing Sheets

Specification includes a Sequence Listing.

(56) References Cited

OTHER PUBLICATIONS

HawkZ05 Fast One-Step RT-PCR Kit, Roche Diagnostics Insert (2010).
Hoffmann et al., "A universal heterologous internal control system for duplex real-time RT-PCR assays used in a detection system for pestiviruses", Journal of Virological Methods, 136:200-209 (2006).
Imboden et al., "Simultaneous Detection of DNA and RNA by Differential Polymerase Chain Reaction (DIFF-PCR)", PCR Methods and Applications, 3:23-27 (1993).
Isenbarger et al., "The Most Conserved Genome Segments for Life Detection on Earth and Other Planets", Orig. Life Evol Biosph (2008).
Lion, "Current Recommendations for positive controls in RT-PCR assays", Leukemia, 15:1033-1037 (2001).
Meng et al., "Automated Multiplex Assay System for Simultaneous Detection of Hepatitis B Virus DNA, Hepatitis C Virus RNA, and Human Immunodeficiency Virus Type 1 RNA", Journal of Clinical Microbiology, 39(8):2937 (2001).
Malhotra-Kumar et al., "Multiplex PCR for Simultaneous Detection of Macrolide and Tetracycline Resistance Determinants in Streptococci", Antimicrob. Agents Chemother., 49(11):4798 (2005).
Hedges et al., "A Comprehensive Set of In Vitro Transcribed RNAs as Controls for Leukemia Molecular Diagnostics", Blood (ASH Annual Meeting Abstracts), 106, Abstract 4528 (2005).
Manual for Fast-track Diagnostics, "Qualitative assay for in vitro diagnostics" (2012).
Singh et al., "Simultaneous amplification of DNA and RNA virus suing multiplex PCR system", Clinica Chimica Acta. 308:179-181 (2001).
AB Applied Biosystems, "VetMAX™-Plus qPCR Master Mix" (2010).
Xu et al., "Development of multiplex PCR for simultaneous detection of six swine DNA and RNA viruses", Journal of Virological Methods, 183:69-74 (2012).
Zimmermann et al., Technical Aspects of Quantitative Competitive PCR, BioTechniques, 21:268-279 (1996).
Willey et al., "Expression Measurement of Many Genes Simultaneously by Quantitative RT-PCR Using Standardized Mixtures of Competitive Templates", Am. J. Respir. Cell Mol. Biol., 19:6-17 (1998).
International Search Report for corresponding application No. PCT/US2013/065681, dated May 12, 2014.

* cited by examiner

```
RNA_IPC    GGCUCCAGGAU--UGCUCUCUUCAGGUAUCUCCCCUCUUUGAGAAGGGCCACAUCCCUACUU
DNA_IPC    AGA--CAAGCTGGTGGCCTGAAAGAATCTCCCCTCTTTGAGAAGGGCCACATCCCTACTT
              *   ***  ** ** * * ************************************

RNA_IPC    CUAGUUUCAGCUGGAAAGGCUU
DNA_IPC    CTAGTTTCAGCTGGAAAGGCTT
           ********************
```

Figure 1A: Nucleic acid sequence for RNA IPC and DNA IPC. The RNA IPC is SEQ ID NO:1. The DNA IPC is SEQ ID NO:2.

RNA IPC Forward primer          5'-GCTCCAGGATTGCTCTTCAGGT-3' (SEQ ID NO:3)
DNA IPC Forward primer          5'-GACAAGCTGGTGGCCTGAAAG-3' (SEQ ID NO:4)
Conserved hydrolysis probe      5'-CTCCCCTCTTTGAGAAGGGCCACATC-3' (SEQ ID NO:5)
Conserved reverse primer        5'-AGCCTTTCCAGCTGAAACTAGAAGTAG-3' (SEQ ID NO:6)

M. gallisepticum forward        5'-CTGGGTTGATTGTTGTTTCTTTACTCTT-3' (SEQ ID NO:7)
M. gallisepticum probe          5'-CTTAGCGATCGGAATCCCAATCCCTAAACC-3' (SEQ ID NO:8)
M. gallisepticum reverse        5'-ACGTTCTTGGATCATCATTCTTTCTT-3' (SEQ ID NO:9)

Component toolbox

| Sequence | Forward | Probe | Reverse |
|---|---|---|---|
| I | 1 | 1 | 1 |
| II | 2 | 2 | 2 |
| III | 3 | 3 | 3 |

FIGURE 2 B

DNA IPC

| | | | | |
|---|---|---|---|---|
| Pair 1: | DNA- A | DNA-1 | DNA-3 | DNA-1 |
| Pair 2: | DNA- B | DNA-1 | DNA-1 | DNA-3 |
| Pair 3: | DNA- C | DNA-2 | DNA-3 | DNA-1 |

RNA IPC

| | | | | |
|---|---|---|---|---|
| Pair 1: | RNA-A | RNA-3 | RNA-3 | RNA-1 |
| Pair 2: | RNA-B | RNA-1 | RNA-2 | RNA-3 |
| Pair 3: | RNA-C | RNA-2 | RNA-3 | RNA-2 |

Figure 3A

Detection Mix

RNA Master Mix

DNA Master Mix

Pooled Positive Control
Contains controls for all assays and optionally a Signature Sequence Internal Positive Control DNA & RNA pair Optional Quality Control Detection Mixes

| RNA Mastermix | DNA Mastermix |

Detection Mix

(with pooled assay specific, and ISC specific, primers and probes)

Pooled Positive Control

---

Optional Quality Control Reagents prokaryotic environmental contamination DMx Signature Sequence DMx

IPC

IPC DMx

Figure 3B

Signature Sequence

Signature Sequence (template)

CTCCACTTCAGGTATCACTCAGTTTGAACTGCAAGACAAGCTGAAAGAATCTCGAGAAGGCC
ACTTCTAGTTTCAGGCTTGGGCACAGCAGATGAAAATAAAGAAGAAAGGACCAGGCCAAGG
CTACAGGCCAAAGAT (SEQ ID NO:11)

Length: 140 nt

Signature Sequence primers:

IDEXXsig-67f    CAAGCTGAAAGAATCTCGAGAAGG (SEQ ID NO:12)
IDEXXsig-149r    CTGGTCCTTCTTTCTTTATTTTCATC (SEQ ID NO:13)

PCR product length: 83 bp

Signature Sequence probe:

IDEXXsig-92p    CCACTTCTAGTTTCAGGCTTGGGCACAG (SEQ ID NO:14)

HMBS1

GAAUGAAGUGGACCUAGUUGUUCAUUCGCUGAAGGACCUGCCCACGGUGCUUCCUCCUGG
CUUCACCAUUGGAGCUGCUGCAAGCGGGAGAGCCCCUAUGAUGCUGUGUCUUUCACCC
AAAAUUUGUUGGGAAGACUCUAGAAACCUUGCCAGAGAAGAGUGUGGUAGGAACUAGCUC
CCU

Figure 5B

HMBS1 Minimer

GAAUGAAGUGGACCUAGUUGUUCAUUCCGUGCUUCCUCCUGGCUUCACCUAGAAGAGUGU
GGUAGGAACUAGCUCCCU

Figure 5A-B. Hypothetical target amplicons for *Bos taurus hmbs1* mRNA. Primer binding sites are underlined. The positive strand probe binding site is double underlined. A. Wild type sequence for *Bos taurus hmbs1* mRNA; the amplicon length is 166 bases (SEQ ID NO:21). B. Modified target amplicon with intervening sequences removed. The total length of the minimer is 78 bases. The amplicon length of the minimer is 61 bases (SEQ ID NO:22).

Figure 6A. Amplification curves from a synthetic minimer RNA control for BVDV.

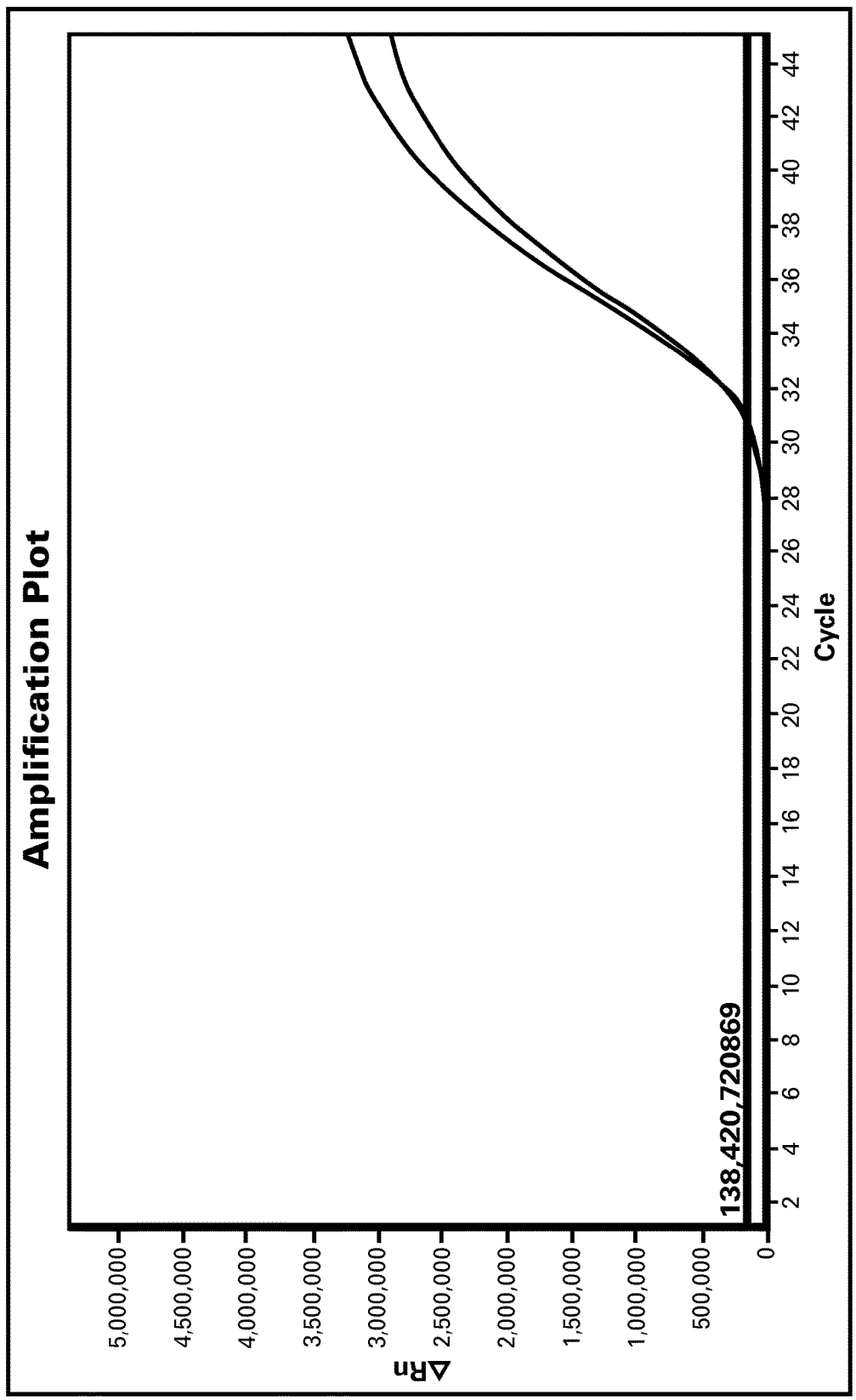
Figure 6B. Amplification curves from a full length DNA oligomer (amplicon size of 206 bases).

SEQUENCE LISTING

<160> NUMBER OF SEQ ID NOS: 22

<210> SEQ ID NO 1
<211> LENGTH: 80
<212> TYPE: RNA
<213> ORGANISM: Unknown
<220> FEATURE:
<223> OTHER INFORMATION: RNA Internal Positive Control

<400> SEQUENCE: 1
ggcuccagga uugcucuuca gguaucuccc cucuuugaga agggccacau cccuacuucu    60
aguuucagcu ggaaaggcuu                                               80

<210> SEQ ID NO 2
<211> LENGTH: 80
<212> TYPE: DNA
<213> ORGANISM: Unknown
<220> FEATURE:
<223> OTHER INFORMATION: DNA Internal Positive Control

<400> SEQUENCE: 2
agacaagctg gtggcctgaa agaatctccc ctctttgaga agggccacat ccctacttct    60
agtttcagct ggaaaggctt                                               80

<210> SEQ ID NO 3
<211> LENGTH: 22
<212> TYPE: DNA
<213> ORGANISM: Unknown
<220> FEATURE:
<223> OTHER INFORMATION: RNA Internal Positive Control forward primer

<400> SEQUENCE: 3
gctccaggat tgctcttcag gt                                            22

<210> SEQ ID NO 4
<211> LENGTH: 21
<212> TYPE: DNA
<213> ORGANISM: Unknown
<220> FEATURE:
<223> OTHER INFORMATION: DNA Internal Positive Control forward primer

<400> SEQUENCE: 4
gacaagctgg tggcctgaaa g                                             21

<210> SEQ ID NO 5
<211> LENGTH: 26
<212> TYPE: DNA
<213> ORGANISM: Unknown
<220> FEATURE:
<223> OTHER INFORMATION: Conserved hydrolysis probe

<400> SEQUENCE: 5
ctcccctctt tgagaagggc cacatc                                        26

<210> SEQ ID NO 6
<211> LENGTH: 27
<212> TYPE: DNA
<213> ORGANISM: Unknown
<220> FEATURE:
<223> OTHER INFORMATION: Conserved reverse primer

<400> SEQUENCE: 6
agcctttcca gctgaaacta gaagtag                                       27

<210> SEQ ID NO 7
<211> LENGTH: 28
<212> TYPE: DNA
<213> ORGANISM: Mycoplasma gallisepticum

<400> SEQUENCE: 7
ctgggttgat tgttgtttct ttactctt 28

<210> SEQ ID NO 8
<211> LENGTH: 30
<212> TYPE: DNA
<213> ORGANISM: Mycoplasma gallisepticum

<400> SEQUENCE: 8
cttagcgatc ggaatcccaa tccctaaacc 30

<210> SEQ ID NO 9
<211> LENGTH: 26
<212> TYPE: DNA
<213> ORGANISM: Mycoplasma gallisepticum

<400> SEQUENCE: 9
acgttcttgg atcatcattc tttctt 26

<210> SEQ ID NO 10
<211> LENGTH: 20
<212> TYPE: DNA
<213> ORGANISM: Unknown
<220> FEATURE:
<223> OTHER INFORMATION: T7 phage promoter

<400> SEQUENCE: 10
taatacgact cactataggg 20

<210> SEQ ID NO 11
<211> LENGTH: 140
<212> TYPE: DNA
<213> ORGANISM: Unknown
<220> FEATURE:
<223> OTHER INFORMATION: Artificial Signature Sequence

<400> SEQUENCE: 11
ctccacttca ggtatcactc agtttgaact gcaagacaag ctgaaagaat ctcgagaagg 60
gccacttcta gtttcaggct tgggcacagc agatgaaaat aaagaaagaa aggaccaggc 120
caaggctaca ggccaaagat 140

<210> SEQ ID NO 12
<211> LENGTH: 24
<212> TYPE: DNA
<213> ORGANISM: Unknown
<220> FEATURE:
<223> OTHER INFORMATION: Primer for artificial Signature Sequence

<400> SEQUENCE: 12
caagctgaaa gaatctcgag aagg 24

<210> SEQ ID NO 13
<211> LENGTH: 27
<212> TYPE: DNA
<213> ORGANISM: Unknown
<220> FEATURE:
<223> OTHER INFORMATION: Primer for artificial Signature Sequence

<400> SEQUENCE: 13

```
ctggtcctttt ctttctttat tttcatc                                    27

<210> SEQ ID NO 14
<211> LENGTH: 28
<212> TYPE: DNA
<213> ORGANISM: Unknown
<220> FEATURE:
<223> OTHER INFORMATION: Probe for artificial Signature Sequence

<400> SEQUENCE: 14
ccacttctag tttcaggctt gggcacag                                    28

<210> SEQ ID NO 15
<211> LENGTH: 26
<212> TYPE: DNA
<213> ORGANISM: Unknown
<220> FEATURE:
<223> OTHER INFORMATION: Artificial primer for eukaryotic 18S DNA

<400> SEQUENCE: 15
gattaagcca tgcatgtcta agtacg                                      26

<210> SEQ ID NO 16
<211> LENGTH: 28
<212> TYPE: DNA
<213> ORGANISM: Unknown
<220> FEATURE:
<223> OTHER INFORMATION: Artificial primer for eukaryotic 18S DNA

<400> SEQUENCE: 16
caaaggaacc ataactgatt taatgagc                                    28

<210> SEQ ID NO 17
<211> LENGTH: 24
<212> TYPE: DNA
<213> ORGANISM: Unknown
<220> FEATURE:
<223> OTHER INFORMATION: Artificial probe for eukaryotic 18S DNA

<400> SEQUENCE: 17
cacggccggt acagtgaaac tgcg                                        24

<210> SEQ ID NO 18
<211> LENGTH: 20
<212> TYPE: DNA
<213> ORGANISM: Unknown
<220> FEATURE:
<223> OTHER INFORMATION: Artificial primer for bacterial 16S ribosomal
      DNA

<400> SEQUENCE: 18
ggatgatcag ccacactgga                                             20

<210> SEQ ID NO 19
<211> LENGTH: 21
<212> TYPE: DNA
<213> ORGANISM: Unknown
<220> FEATURE:
<223> OTHER INFORMATION: Artificial primer for bacterial 16S ribosomal
      DNA

<400> SEQUENCE: 19
ccaatattcc tcactgctgc c                                           21

<210> SEQ ID NO 20
<211> LENGTH: 26
```

```
<212> TYPE: DNA
<213> ORGANISM: Unknown
<220> FEATURE:
<223> OTHER INFORMATION: Artificial probe for bacterial 16S ribosomal
      DNA

<400> SEQUENCE: 20
cccgtaggag tctggaccgt gtctca                                              26

<210> SEQ ID NO 21
<211> LENGTH: 183
<212> TYPE: RNA
<213> ORGANISM: Bos taurus

<400> SEQUENCE: 21
gaaugaagug gaccuaguug uucauucgcu gaaggaccug cccacggugc uuccuccugg         60
cuucaccauu ggagcugucu gcaagcggga gagccccuau gaugcuguug ucuuucaccc        120
aaaauuuguu gggaagacuc uagaaaccuu gccagagaag agugugguag gaacuagcuc        180
ccu                                                                      183

<210> SEQ ID NO 22
<211> LENGTH: 78
<212> TYPE: RNA
<213> ORGANISM: Bos taurus

<400> SEQUENCE: 22
gaaugaagug gaccuaguug uucauuccgu gcuuccuccu ggcuucaccu agaagagugu         60
gguaggaacu agcucccu                                                       78
```

NUCLEIC ACID AMPLIFICATION CONTROLS AND KITS AND METHODS OF USE THEREOF

This application claims the benefit of U.S. Ser. No. 61/715,596 filed Oct. 18, 2012, and U.S. Ser. No. 61/790,854 filed Mar. 15, 2013, both of which are incorporated by reference herein in their entirety.

BACKGROUND

Real time PCR has created a revolution in diagnostics, with increased speed, sensitivity and specificity over many other offerings. The components of real time PCR tests can include, e.g., i) master mix (containing enzyme, buffer, and nucleotides), ii) positive controls, iii) internal positive controls (to ensure proper nucleic acid purification), iv) detection mix (containing the target-specific primers and probes), v) internal sample control; or vi) combinations thereof. The instant invention provides PCR systems, including real-time PCR systems, in which all tests and testing protocols are standardized. The goal of this platform is to minimize both handling of material and time spent running samples. For example, a single Internal Positive Control (IPC) can provide a means to ensure proper nucleic acid purification for both RNA and DNA test targets. Additionally, standard cycling conditions for all diagnostic tests allow the user to run both RNA and DNA targets side-by-side on the same reaction plate. The assays will run in approximately one hour, or less. A number of real time PCR tests have been developed on the new platform. Analytical sensitivity analysis for IDEXX RealPCR *Mycoplasma gallisepticum, M. synoviae*, Bovine Viral Diarrhea Virus (BVDV), Bluetongue Virus (BTV), and *Mycobacterium avium* subspecies *paratuberculosis* (MAP) tests each demonstrate sensitivity of ≤10 copies per reaction with high specificity and compatibly for use with one or more internal positive controls and/or internal sample controls. Standardized protocols and components in the test system will provide laboratories a more efficient and flexible platform for PCR testing, including real-time PCR, that will greatly minimize component handling, simplify workflows, reduce the likelihood of operator error, and reduce total testing time.

SUMMARY OF THE INVENTION

One embodiment of the invention provides a nucleic acid amplification kit. The kit comprises:
 (a) a master mix comprising one or more DNA polymerases, nucleoside triphosphates, and optionally one or more reverse transcriptases;
 (b) a pooled target positive control comprising two or more target positive control polynucleotides for two or more target polynucleotides and one or more signature sequence polynucleotides; and
 (c) an internal sample control detection mix comprising one or more forward primers, one or more reverse primers, and one or more probes that can amplify and detect one or more conserved eukaryotic polynucleotides The one or more DNA polymerases can be combined with one or more reverse transcriptase polymerases. The kit can further comprise an assay specific target polynucleotide detection mix comprising one or more assay specific forward primers, one or more assay specific reverse primers, and one or more assay specific probes.

The pooled target positive control can comprise 10, 20, 30 or more target positive control polynucleotides for 10, 20, 30 or more target polynucleotides. The kit can further comprising a quality control detection mix comprising one or more of: (a) an internal positive control polynucleotide pair comprising a DNA internal positive control (IPC) polynucleotide and a RNA internal positive control (IPC) polynucleotide, wherein the DNA IPC and the RNA IPC share one or two same or similar forward primer binding regions, probe binding regions, or reverse primer binding regions, and wherein one or two of the forward primer binding regions, probe binding regions, or reverse primer binding regions of the DNA IPC and the RNA IPC are different; and
 (b) PanB detection mix comprising one or more forward primers, one or more reverse primers and one or more probes that can amplify and detect one or more conserved prokaryotic polynucleotides.

The assay specific target polynucleotide detection mix can further comprises one or more internal positive control forward primers, one or more internal positive control reverse primers, and one or more internal positive control probes. The master mix, pooled target positive control, and internal positive control polynucleotide pair can be universal components that can be used with any assay specific target polynucleotide detection mix. The assay specific polynucleotide detection mix can comprise assay specific reverse primers, assay specific forward primers, and one or more assay specific probes for two or more different target polynucleotides. The two or more different target polynucleotides can comprise RNA polynucleotides and DNA polynucleotides. The master mix, pooled target positive control and internal sample control detection mix can be used to amplify both DNA polynucleotide targets and RNA polynucleotide targets on the same multiwell device. One or more of the pooled target positive control polynucleotides can comprise a forward primer binding region, a probe binding region, and a reverse primer binding region, wherein each of the primer binding region, the probe binding region, and the reverse primer binding region have homology to a corresponding forward primer binding region, a probe binding region and a reverse primer binding region in a target polynucleotide, and wherein the one or more of the pooled target positive control polynucleotides can have 10 or more fewer nucleic acid bases than a region of the target polynucleotide comprising the forward primer binding region, the probe binding region, the reverse primer binding region and any intervening regions for which the target positive control polynucleotides serve as a control.

Another embodiment of the invention provides a method for performing a polymerase chain reaction. The method comprises loading one or more vessels with:
 (a) a test sample;
 (b) an internal sample control detection mix comprising one or more forward primers, one or more reverse primers, and one or more probes that can amplify and detect one or more conserved eukaryotic polynucleotides;
 (c) an assay specific target polynucleotide detection mix for a DNA target polynucleotide comprising one or more assay specific forward primers, one or more assay specific reverse primers, and one or more assay specific probes; or an assay specific target polynucleotide detection mix for a RNA target polynucleotide comprising one or more assay specific forward primers, one or more assay specific reverse primers, and one or more assay specific probes; or a combined detection mix for DNA and RNA target polynucleotides; and (d) master mix comprising one or more DNA polymerases, nucleoside triphosphates, and optionally one or more reverse transcriptases.

The one or more vessels are subjected to universal polymerase chain reaction thermocycling conditions at the same time in the same thermocycler. The one or more vessels can be loaded with both an assay specific target polynucleotide detection mix for a DNA target polynucleotide and with an assay specific target polynucleotide detection mix for a RNA target polynucleotide. The one or more vessels can further be loaded with:

(a) pooled target positive control polynucleotides or a single target positive control polynucleotide;
(b) a signature sequence;
(c) an assay specific target polynucleotide detection mix for a DNA target polynucleotide comprising one or more assay specific forward primers, one or more assay specific reverse primers, and one or more assay specific probes; or an assay specific target polynucleotide detection mix for a RNA target polynucleotide comprising one or more assay specific forward primers, one or more assay specific reverse primers, and one or more assay specific probes; or a combined detection mix for DNA and RNA target; and
(d) master mix comprising one or more DNA polymerases, nucleoside triphosphates, and optionally one or more reverse transcriptases.

One or more additional vessels can be loaded with:
(a) water or buffer;
(b) an assay specific target polynucleotide detection mix for a DNA target polynucleotide comprising one or more assay specific forward primers, one or more assay specific reverse primers, and one or more assay specific probes; or an assay specific target polynucleotide detection mix for a RNA target polynucleotide comprising one or more assay specific forward primers, one or more assay specific reverse primers, and one or more assay specific probes; or a combined detection mix for DNA and RNA target; and
(c) master mix comprising one or more DNA polymerases, nucleoside triphosphates, and optionally one or more reverse transcriptases.

One or more additional vessels can be loaded with:
(a) a test sample;
(b) a DNA internal positive control (IPC), an RNA internal positive control (IPC), or both a DNA and an RNA internal positive control, wherein the DNA IPC and the RNA IPC share one or two same or similar forward primer binding regions, probe binding regions, or reverse primer binding regions, and wherein one or two of the forward primer binding regions, probe binding regions, or reverse primer binding regions of the DNA IPC and the RNA IPC are different;
(c) internal positive control detection mix comprising one or more internal positive control forward primers, one or more internal positive control reverse primers, and one or more internal positive control probes; and
(d) master mix comprising one or more DNA polymerases, nucleoside triphosphates, and optionally one or more reverse transcriptases.

One or more of the target positive control polynucleotides can comprise a forward primer binding region, a probe binding region, and a reverse primer binding region, wherein each of the primer binding region, the probe binding region, and the reverse primer binding region have homology to a corresponding forward primer binding region, a probe binding region and a reverse primer binding region in a target polynucleotide, and wherein one or more of the pooled target positive control polynucleotides can have 10 or more fewer nucleic acid bases than a region of the target polynucleotide comprising the forward primer binding region, the probe binding region, the reverse primer binding region and any intervening regions for which the target positive control polynucleotides serve as a control.

One or more additional vessels can be loaded with:
(a) a sample to be tested for contamination;
(b) detection mix for a signature sequence; and
(c) master mix comprising one or more DNA polymerases, nucleoside triphosphates, and optionally one or more reverse transcriptases.

One or more additional vessels can be loaded with:
(a) a sample to be tested for contamination or a test sample;
(b) PanB detection mix comprising one or more forward primers, one or more reverse primers, and one or more probes that can amplify and detect one or more conserved prokaryotic polynucleotides; and
(c) master mix comprising one or more DNA polymerases, nucleoside triphosphates, and optionally one or more reverse transcriptases.

The universal polymerase chain reaction thermocycling conditions can be 40-65° C. for 10-30 minutes; then about 45 cycles of 94-95° C. for 5-15 seconds, and 60° C. for 20-45 seconds. The polymerase chain reaction can be a real-time polymerase chain reaction.

Still another embodiment provides a mixture of nucleic acid amplification reagents. The reagents can comprise:
(a) a master mix comprising one or more DNA polymerases, nucleoside triphosphates, and optionally one or more reverse transcriptases;
(b) an assay specific target polynucleotide detection mix comprising one or more assay specific forward primers, one or more assay specific reverse primers, and one or more assay specific probes; and
(c) an internal sample control detection mix comprising one or more forward primers, one or more reverse primers, and one or more probes that can amplify and detect one or more conserved eukaryotic polynucleotides;

wherein each of (a), (b), and (c) are each individual mixtures; or wherein one or more of (a), (b), and (c) are combined together into one or more mixtures; or wherein (a), (b), and (c) are combined together in a single mixture.

The one or more DNA polymerases can be combined reverse transcriptase PCR DNA polymerases. The mixture can further comprise a pooled target positive control comprising two or more target positive control polynucleotides for two or more target polynucleotides and one or more signature sequence polynucleotides, wherein the pooled positive control is an individual mixture or is combined with one or more of (a), (b) or (c). The pooled target positive control can comprise 10, 20, 30 or more target positive control polynucleotides for 10, 20, 30 or more target polynucleotides. The mixture can further comprise a quality control detection mix comprising one or more of:

(a) an internal positive control polynucleotide pair comprising a DNA internal positive control (IPC) polynucleotide and a RNA internal positive control (IPC) polynucleotide, wherein the DNA IPC and the RNA IPC share one or two same or similar forward primer binding regions, probe binding regions, or reverse primer binding regions, and wherein one or two of the forward primer binding regions, probe binding regions, or reverse primer binding regions of the DNA IPC and the RNA IPC are different;
(b) a signature sequence; and
(c) PanB detection mix comprising one or more forward primers, one or more reverse primers and one or more probes that can amplify and detect one or more conserved prokaryotic polynucleotides.

The assay specific target polynucleotide detection mix can further comprise one or more internal positive control forward primers, one or more internal positive control reverse primers, and one or more internal positive control probes. The master mix, pooled target positive control, and internal sample control detection mix can be universal components that can be used with any assay specific target polynucleotide detection mix. The assay specific target polynucleotide detection mix can comprise assay specific reverse primers, assay specific forward primers, and one or more assay specific probes for two or more different target polynucleotides. The two or more different target polynucleotides can comprise RNA polynucleotides and DNA polynucleotides. The master mix, pooled target positive control and internal sample control detection mix can be used to amplify both DNA polynucleotide targets and RNA polynucleotide targets on the same multiwell device.

Even another embodiment of the invention provides nucleic acid composition for use in polymerase chain reaction amplification. The composition comprises:
an internal positive control (IPC) DNA polynucleotide and an internal positive control (IPC) RNA polynucleotide, wherein the DNA and RNA polynucleotides each comprise a forward primer binding region, a reverse primer binding region, and a probe binding region, wherein the DNA and RNA polynucleotides share the same or similar one or two sequence elements selected from the group consisting of:
a forward primer binding region
a reverse primer binding region, and
a probe binding region;
and wherein the DNA and RNA polynucleotides have different one or two sequence elements selected from the group consisting of:
a forward primer binding region
a reverse primer binding region, and
a probe binding region.

The nucleic acid composition can further comprise:
a forward primer capable of supporting amplification of both the DNA polynucleotide and a reverse transcript of the RNA polynucleotide,
a reverse primer capable of supporting amplification of the DNA polynucleotide, but not of the reverse transcript of the RNA polynucleotide,
a probe capable of supporting the detection of amplification products of both the DNA polynucleotide and of the reverse transcript of the RNA polynucleotide.

The nucleic acid composition can further comprise:
a forward primer capable of supporting amplification of the DNA polynucleotide, but not of a reverse transcript of the RNA polynucleotide,
a reverse primer capable of supporting amplification of both the DNA polynucleotide and of the reverse transcript of the RNA polynucleotide,
a probe capable of supporting the detection of amplification products of both the DNA polynucleotide and the reverse transcript of RNA polynucleotide.

The nucleic acid composition can further comprise:
a forward primer capable of supporting amplification of both the DNA polynucleotide and of the reverse transcript of the RNA polynucleotide,
a reverse primer capable of supporting amplification of both the DNA polynucleotide and of the reverse transcript of the RNA polynucleotide,
a probe capable of supporting the detection of amplification products of the DNA polynucleotide, but not of the reverse transcript of RNA polynucleotide.

The nucleic acid composition can further comprise:
a forward primer capable of supporting amplification of both the DNA polynucleotide and a reverse transcript of the RNA polynucleotide,
a reverse primer capable of supporting amplification of the reverse transcript of the RNA polynucleotide, but not of the DNA polynucleotide,
a probe capable of supporting the detection of amplification products of both the DNA polynucleotide and of the reverse transcript of the RNA polynucleotide.

The nucleic acid composition can further comprise:
a forward primer capable of supporting amplification of a reverse transcript of the RNA polynucleotide, but not of the DNA polynucleotide,
a reverse primer capable of supporting amplification of both the DNA polynucleotide and of the reverse transcript of the RNA polynucleotide,
a probe capable of supporting the detection of amplification products of both the DNA polynucleotide and the reverse transcript of RNA polynucleotide.

The nucleic acid composition can further comprise:
a forward primer capable of supporting amplification of both the DNA polynucleotide and of a reverse transcript of the RNA polynucleotide,
a reverse primer capable of supporting amplification of both the DNA polynucleotide and of the reverse transcript of the RNA polynucleotide,
a probe capable of supporting the detection of amplification products of the reverse transcript of RNA polynucleotide, but not of the DNA polynucleotide.

Yet another embodiment of the invention provides a polymerase chain reaction control ribonucleic acid molecule comprising a forward primer binding region, a probe binding region, and a reverse primer binding region, wherein each of the primer binding region, the probe binding region, and the reverse primer binding region have homology to a corresponding forward primer binding region, a probe binding region and a reverse primer binding region in a target polynucleotide, and wherein the polymerase chain reaction control ribonucleic acid molecule can have 10 or more fewer nucleic acid bases than a region of the target polynucleotide comprising the forward primer binding region, the probe binding region, the reverse primer binding region and any intervening regions for which the polymerase chain reaction control ribonucleic acid molecule serves as a control. The polymerase chain reaction control ribonucleic acid molecule can have 2 or more fewer nucleic acid bases between the forward primer binding region and the probe binding region than occurs in the target polynucleotide and wherein the polymerase chain reaction control ribonucleic acid molecule can have 2 or more fewer nucleic acid bases between the probe primer binding region and the reverse binding region than occurs in the target polynucleotide. The polymerase chain reaction control ribonucleic acid molecule can have between about 5 and 15 nucleic acid bases 5' to the forward primer binding site and between about 5 and 15 nucleic acid bases 3' to the reverse primer binding site that have homology to the target polynucleotide.

Another embodiment of the invention provides a pooled target positive control composition comprising two or more target positive control polynucleotides for two or more target polynucleotides and one or more signature sequence polynucleotides. The composition can comprise 5, 10, 15, 20, 50 or more target positive control polynucleotides for 5, 10, 15, 20, 50 or more target polynucleotides. The two or more target positive control polynucleotides for two or more target polynucleotides can comprise both DNA and RNA target positive control polynucleotides. The one or more of the target positive control polynucleotides can be control ribonucleic acid molecules comprising a forward primer binding region, a probe binding region, and a reverse primer binding region, wherein each of the primer binding region, the probe binding region, and the reverse primer binding region have homology to a corresponding forward primer binding region, a probe binding region and a reverse primer binding region in a target polynucleotide, and wherein the polymerase chain reaction control ribonucleic acid molecule can have 10 or more fewer nucleic acid bases than a region of the target polynucleotide comprising the forward primer binding region, the probe binding region, the reverse primer binding region and any intervening regions for which the polymerase chain reaction control ribonucleic acid molecule serves as a control. The molar concentration of the one or more signature sequence polynucleotides can be greater than the molar concentration of one or more of the target positive control polynucleotides.

Yet another embodiment of the invention provides a method of testing for contamination of a PCR sample. The method comprises loading one or more vessels with:
  (a) a sample to be tested for contamination;
  (b) detection mix for a signature sequence; and
  (c) master mix comprising one or more DNA polymerases, nucleoside triphosphates, and optionally one or more reverse transcriptases. The one or more vessels are subjected to polymerase chain reaction conditions.

Still another embodiment of the invention provides a method for performing a polymerase chain reaction that amplifies both a DNA target polynucleotide and an RNA target polynucleotide on the same multiwell device. The method comprises loading two or more vessels on the same multiwell device with:
  (a) a test sample;
  (b) an internal sample control detection mix comprising one or more forward primers, one or more reverse primers, and one or more probes that can amplify and detect one or more conserved eukaryotic polynucleotides;
  (c) an assay specific target polynucleotide detection mix for a DNA target polynucleotide comprising one or more assay specific forward primers, one or more assay specific reverse primers, and one or more assay specific probes and an assay specific target polynucleotide detection mix for a RNA target polynucleotide comprising one or more assay specific forward primers, one or more assay specific reverse primers, and one or more assay specific probes; or a combined detection mix for DNA and RNA target polynucleotides; and
  (d) master mix comprising one or more DNA polymerases, nucleoside triphosphates, and one or more reverse transcriptases.

The two or more vessels on the same multiwell device are subjected to universal polymerase chain reaction thermocycling conditions at the same time in the same thermocycler. The two or more vessels can be loaded with both an assay specific target polynucleotide detection mix for a DNA target polynucleotide and with an assay specific target polynucleotide detection mix for a RNA target polynucleotide. One or more additional vessels on the multiwell device can be loaded with:
  (a) pooled target positive control polynucleotides or a single target positive control polynucleotide;
  (b) a signature sequence;
  (c) an assay specific target polynucleotide detection mix for a DNA target polynucleotide comprising one or more assay specific forward primers, one or more assay specific reverse primers, and one or more assay specific probes; or an assay specific target polynucleotide detection mix for a RNA target polynucleotide comprising one or more assay specific forward primers, one or more assay specific reverse primers, and one or more assay specific probes; or a combined detection mix for DNA and RNA target; and
  (d) master mix comprising one or more DNA polymerases, nucleoside triphosphates, and optionally one or more reverse transcriptases.

One or more additional vessels on the multiwell device can be loaded with:
  (a) water or buffer;
  (b) an assay specific target polynucleotide detection mix for a DNA target polynucleotide comprising one or more assay specific forward primers, one or more assay specific reverse primers, and one or more assay specific probes; or an assay specific target polynucleotide detection mix for a RNA target polynucleotide comprising one or more assay specific forward primers, one or more assay specific reverse primers, and one or more assay specific probes; or a combined detection mix for DNA and RNA target; and
  (c) master mix comprising one or more DNA polymerases, nucleoside triphosphates, and optionally one or more reverse transcriptases.

One or more additional vessels on the multiwell device can be loaded with:
  (a) a test sample;
  (b) a DNA internal positive control (IPC), an RNA internal positive control (IPC), or both a DNA and an RNA internal positive control, wherein the DNA IPC and the RNA IPC share one or two same or similar forward primer binding regions, probe binding regions, or reverse primer binding regions, and wherein one or two of the forward primer binding regions, probe binding regions, or reverse primer binding regions of the DNA IPC and the RNA IPC are different;
  (c) internal positive control detection mix comprising one or more internal positive control forward primers, one or more internal positive control reverse primers, and one or more internal positive control probes; and
  (d) master mix comprising one or more DNA polymerases, nucleoside triphosphates, and optionally one or more reverse transcriptases.

The one or more of the target positive control polynucleotides can comprise a forward primer binding region, a probe binding region, and a reverse primer binding region, wherein each of the primer binding region, the probe binding region, and the reverse primer binding region have homology to a corresponding forward primer binding region, a probe binding region and a reverse primer binding region in a target polynucleotide, and wherein one or more of the pooled target positive control polynucleotides can have or more fewer nucleic acid bases than a region of the target polynucleotide comprising the forward primer binding region, the probe binding region, the reverse primer binding region and any intervening regions for which the target positive control polynucleotides serve as a control.

One or more additional vessels on the multiwell device can be loaded with:
(a) a sample to be tested for contamination;
(b) detection mix for a signature sequence; and
(c) master mix comprising one or more DNA polymerases, nucleoside triphosphates, and optionally one or more reverse transcriptases.

One or more additional vessels on the multiwell device can be loaded with:
(a) a sample to be tested for contamination or a test sample;
(b) PanB detection mix comprising one or more forward primers, one or more reverse primers, and one or more probes that can amplify and detect one or more conserved prokaryotic polynucleotides; and
(c) master mix comprising one or more DNA polymerases, nucleoside triphosphates, and optionally one or more reverse transcriptases.

The universal polymerase chain reaction thermocycling conditions can be 40-65° C. for 10-30 minutes; then about 45 cycles of 94-95° C. for 5-15 seconds, and 60° C. for 20-45 seconds. The polymerase chain reaction can be a real-time polymerase chain reaction.

BRIEF DESCRIPTION OF THE DRAWINGS

FIG. 1A shows nucleic acid sequences of an example of an RNA internal positive control and a DNA internal positive control. FIG. 1B shows primers and probes used in a PCR assay of the invention.

FIG. 2 shows the structure of RNA internal positive controls and DNA internal positive controls.

FIG. 3A-B shows examples of components of a PCR assay kit of the invention.

FIG. 4 shows an example of a signature sequence polynucleotide.

FIG. 5A-B shows hypothetical target amplicons for *Bos taurus* hmbs1. Primer binding sites are underlined. The positive strand probe binding site is double underlined. A. Wild type sequence for *Bos taurus* hmbs1; the amplicon length is 166 bases (SEQ ID NO:21). B. Modified target amplicon with intervening sequences removed. The total length of the minimer is 78 bases. The amplicon length of the minimer is 61 bases (SEQ ID NO:22).

FIG. 6A shows amplification curves from a synthetic minimer RNA control for BVDV.

FIG. 6B shows amplification curves from a full length DNA oligomer for BVDV (amplicon size of 206 bases).

DETAILED DESCRIPTION OF THE INVENTION

As used herein, the singular forms "a," "an", and "the" include plural referents unless the context clearly dictates otherwise.

Real-time PCR permits the specific amplification and detection of targeted DNA or RNA sequences. This technique relies on a primer/probe detection mix that specifically targets a DNA or RNA sequence. In the presence of target nucleic acid, each round of PCR amplification results in an ever increasing signal, for example, a fluorescent signal, that can be optionally detected in real-time. Two concerns must be addressed when choosing real-time PCR (or other PCR methodologies) for diagnostics. Firstly, the potential presence of PCR inhibitors in clinical samples can decrease the efficiency of a reaction leading to false negatives. To monitor such activity, internal positive controls can be employed. Such controls often consist of exogenous DNA or RNA that are added to raw clinical samples prior to purification. During a testing event, signal generation from the internal positive control indicates proper nucleic acid extraction and purification as well as proper amplification. Secondly, while many real-time PCR protocols (or other PCR protocols) finish quickly, a drawback remains that many tests often require a unique cycling protocol, meaning tests must "wait in line" while another test runs. The use of different thermocycling protocols for different tests further requires the operator to switch between different cycling programs which takes time and is a potential source of operator error. The diagnostic tests of the instant invention can use an internal positive control and/or an internal sample control detection mix and utilize a universal cycling protocol. Results for three such tests: BTV, MAP and BVDV are described in the working examples. Standardized protocols and components in the assay systems will provide laboratories a more efficient and flexible platform for PCR methodologies, including real-time PCR methodologies.

Primers and Probes

A primer is a polynucleotide that is capable of hybridizing with a target or control nucleic acid and serves as an initiation site for nucleotide (RNA or DNA) polymerization under suitable conditions (e.g., in the presence of four different nucleoside triphosphates and an thermostable enzyme for polymerization, such as DNA polymerase or reverse transcriptase) in a buffer and at a suitable temperature. A primer need not have the exact sequence of a target or control polynucleotide, but must be sufficiently complementary to hybridize with a polynucleotide. A primer binding site is the region of the target polynucleotide or control polynucleotide to which a primer hybridizes.

A primer anneals to another nucleic acid if the primer, or a portion thereof, hybridizes to a nucleotide sequence within the nucleic acid. A primer can hybridized completely or exclusively to that nucleotide sequence, but a primer need not hybridize either completely or exclusively to that one nucleotide sequence.

Primers are selected so that the majority of the amplicons detected after amplification are full-length. That is, they result from priming at the expected sites at each end of the target polynucleotide or control polynucleotide, as opposed to amplicons resulting from priming within the target polynucleotide or control polynucleotide, which produces shorter than expected amplicons. Primers are selected so that at least 55%, at least 60%, at least 65%, at least 70%, at least 75%, at least 80%, at least 85%, at least 90%, at least 95%, at least 96%, at least 97%, at least 98%, or at least 99% of amplicons are full-length.

A primer pair is a set of primers including a 5' forward primer that hybridizes with the complement of the 5' end of the nucleotide sequence to be amplified and a 3' reverse primer that hybridizes with the 3' end of the nucleotide sequence to be amplified.

The molar ratio of primers to target polynucleotides or control polynucleotides can be from about 500:1 to about 8000:1. Other molar ratios include about 1000:1, about 1100:1, about 1200:1, about 1300:1, about 1400:1, about 1500:1, about 1600:1, about 1700:1, about 1800:1, about 1900:1, about 2000:1, about 2500:1, about 3000:1, about 3500:1, about 4000:1, about 4500:1, about 5000:1, about 5500:1, about 6000:1, about 6500:1, about 7000:1, and about 7500:1.

A probe is a nucleic acid capable of binding to a target or control polynucleotide of complementary sequence through one or more types of chemical bonds, e.g., through hydrogen bond formation, such that a duplex structure is formed. A probe binds or hybridizes to a probe binding site. The probe can be labeled with a detectable label to permit detection of the probe, particularly after the probe has hybridized to its complementary target polynucleotide or control polynucleotide. Alternatively, a probe may be unlabeled, but may be detectable by specific binding with a ligand that is labeled, either directly or indirectly. Moreover, a labeled probe may be detected after being hydrolyzed by an enzyme having an exonuclease activity.

A primer or probe sequence can be 100% complementary to the target sequence or control sequence to which it hybridizes or can be less than 100% complementary. In certain embodiments, a primer or probe sequence has at least 65% identity to the complement of the target nucleic acid sequence or control nucleic acid sequence over a sequence of at least about 5, 6, 7, 8, 9, or 10 nucleotides, more typically over a sequence in the range of 10-30 nucleotides, and often over a sequence of at least 14-25 nucleotides, and more often has at least 75% homology, at least 85% homology, at least 90% homology, or at least 95%, 96%, 97%, 98%, or 99% homology.

The design of primers and probes that hybridize to a specific target polynucleotide or control polynucleotide is within the skill of the art. Primers specific for a target polynucleotide or control polynucleotide should be unique to identify a specific organism, an organism group, or a specific gene (e.g., a gene or polynucleotide of a specific toxin or disease marker). Forward and reverse PCR primers should be able to hybridize with high efficiency and specificity the target polynucleotides or control polynucleotides in the test sample with cross-reactivity to non-target or non-control polynucleotides. Primers can be searched for cross-reactivity with other organisms or genes in, for example, a database such as the National Center for Biotechnology Information database. The target polynucleotide sequence to be amplified should be conserved in the organism. A conserved site should be selected over a site with a high frequency of polymorphisms. The design of primers and probes has been discussed in detail at, for example, Uhl & Cockerill (2004) The fluorescence resonance energy transfer system, p. 295-306. In Persing et al. (ed.), Molecular microbiology diagnostic principles and practice. ASM Press, Washington D.C.; Hyndman & Mitsuhashi (2003) PCR primer design, p. 81-88, In Bartlett & Stirling (ed.), Methods in molecular biology, PCR protocols, 2nd ed. Humana Press, Totowa, N.J. Additionally, primers and probes suitable for PCR are known for many organisms, polynucleotides, and genes.

PCR

Polymerase chain reaction amplification (PCR) is an amplification method in which thermal cycling, consisting of cycles of repeated heating and cooling of the reaction for nucleic acid melting and enzymatic replication of the nucleic acids. PCR thermal cycling protocols are well known in the art. Typically, PCR consists of a series of 20-40 cycles. For example, the cycle may include a denaturation step, an annealing step (allowing annealing of the primers to the single-stranded DNA or RNA template) and an extension/elongation step. Each step may occur at a particular temperature, for a particular length of time, and under particular reaction conditions. For example, the temperature of the denaturation step may be about 80, 85, 90, 94, 95, 96, 97, 98, 99, or 100° C., the temperature of the annealing step may be about 40, 50, 55, 60, 62, 65, or 70° C., and the temperature of the extension/elongation step may be about 40, 50, 55, 60, 65, 70, 72, or 75° C.

A PCR assay may be a real-time polymerase chain reaction, which may be quantitative, and may also be combined with a reverse transcriptase reaction when performing reverse transcription-PCR. Other types of PCR assays that can use the components of the invention include, for example, hot start PCR, reverse transcription polymerase chain reaction, multiplex-polymerase chain reaction, miniprimer polymerase chain reactions, solid phase polymerase chain reaction, touchdown polymerase chain reaction. Combinations of one or more of these techniques can also be used.

Polynucleotides

Polynucleotides of the invention (also referred to herein as nucleic acids, nucleic acid molecules and polynucleotide or nucleic acid sequences, including for example, primers, probes, control polynucleotides, target polynucleotides, forward primer binding regions, probe binding regions, reverse primer binding regions, promoters, or signature sequence), can be single- or double-stranded nucleic acids. A polynucleotide can be RNA, mRNA, DNA, cDNA, genomic DNA or genomic RNA, chemically synthesized RNA or DNA, in vitro transcribed RNA, plasmids, or combinations thereof. The polynucleotides can be purified free of other components, such as proteins, lipids and other polynucleotides. For example, the polynucleotide can be 75%, 90%, 95%, 96%, 97%, 98%, 99%, or 100% purified. A nucleic acid molecule existing among hundreds to millions of other nucleic acid molecules within, for example, cDNA or genomic libraries, or gel slices containing a genomic DNA restriction digest are not to be considered an isolated polynucleotide.

Polynucleotides of the invention can consist of less than about 300, 200, 150, 100, 90, 80, 70, 60, 50, 40, 30, 20, 10, or 5 (or any range between about 5 and about 300) contiguous nucleotides. Polynucleotides of the invention can consist of greater than about 5, 10, 20, 30, 40, 50, 60, 70, 80, 90, 100, 150, 200, 250, or 300 (or any range between about 5 and 300) contiguous nucleotides. Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and *Staphylococcal* protein A.

Polynucleotides of the invention can be isolated. An isolated polynucleotide is a naturally-occurring polynucleotide that is not immediately contiguous with one or both of the 5' and 3' flanking genomic sequences that it is naturally associated with. Isolated polynucleotides also include non-naturally occurring nucleic acid molecules.

Polynucleotides of the invention can be labeled. Suitable labels, and methods for labeling polynucleotides, probes, and primers, are known in the art, and include, for example, radioactive labels incorporated by nick translation or by kinase, biotin labels, fluorescent labels, chemiluminescent labels, bioluminescent labels, metal chelator labels and enzyme labels.

Assay Specific Target Polynucleotide Detection Mix (DMx)

A detection mix contains assay specific primers and probes for amplification and detection of target polynucleotides. "Assay specific" means the primers and probes of the detection mix are designed to amplify one or more known polynucleotide targets (e.g., a portion of a RNA or DNA genome of a particular microorganism or a particular gene or polynucleotide). In one embodiment, a polynucleotide target is a naturally occurring polynucleotide. A polynucleotide target is a polynucleotide that is potentially present in a test sample and for which the assay user desires to know if the polynucleotide is present in the test sample. Assay specific primers and probes for target polynucleotides detect target polynucleotides and positive control target polynucleotides and do not detect other control polynucleotides. A target polynucleotide is not a control polynucleotide. DNA assay specific target polynucleotide detection mix contains one or more primers (forward and reverse) and one or more probes for specific DNA polynucleotide targets and, optionally, one or more primers (forward and reverse) and one or more probes for one or more internal sample controls (ISC). The primers and probes are present in a buffer. A RNA assay specific target polynucleotide detection mix contains one or more primers (forward and reverse) and one or more probes for specific RNA polynucleotide targets and, optionally, one or more primers (forward and reverse) and one or more probes for the one or more ISCs. These primers and probes are optionally present in a RNA-safe buffer having one or more RNase inhibitors. A combined DNA and RNA assay specific target polynucleotide detection mix contains one or more primers (forward and reverse) and one or more probes for one or more specific DNA polynucleotide targets, one or more primers (forward and reverse) and one or more probes for one or more specific RNA polynucleotide targets, and optionally, one or more primers (forward and reverse) and one or more probes for one or more IPCs, and optionally, an RNase-safe buffer.

Several types of probes are suitable for use in the assays of the invention including, for example 5' nuclease probes, FRET hybridization probes, and molecular beacon probes. 5' nuclease probes (hydrolysis probes; TaqMan® probes) are oligonucleotides with a 5' fluorescent dye and 3' quenching dye, or vice versa. To generate a detection signal the effects of the quenching dye on the fluorescent dye must be removed. This is accomplished by (1) the probe binding to the complementary nucleic acid strand and (2) the polymerase (e.g., Taq polymerase) cleaving the 5' end of the 5' nuclease probe.

FRET hybridization probes are a set of two probes that anneal next to each other in a head to tail configuration on the amplified nucleic acid molecule. The upstream probe has a fluorescent dye on the 3' end and the downstream probe has an acceptor dye on the 5' end. Where both probes anneal to the amplified nucleic acid molecule the fluorescence dye is absorbed by the acceptor dye. The acceptor dye is excited and emits light at a third wavelength, which is detected. Where the probes do not bind to amplified nucleic acid molecule FRET does not occur. The downstream probe can be phosphorylated on the 3' end to prevent it from being used as a primer by the polymerase during amplification.

Molecular beacon probes are probes that have a fluorescent dye on the 5' end and a quencher dye on the 3' end of the probe. A region at each end of the probe is complementary to itself, so that at low temperatures the ends anneal creating a hairpin structure. When the ends of the probe are annealed to each other the fluorescence of the reporter dye is quenched. The center region of the probe is complementary to the target nucleic acid or control nucleic acid. At higher temperatures during the PCR assay, the probe binds to the amplified nucleic acid such that the fluorescent reporting dye is separated from the quenching dye. A light signal from the reported dye can then be detected. Where no amplified nucleic acids are available for hybridization, the probe will reanneal to itself causing the quenching of the fluorescent signal. Multiple molecular beacon probes with different reporter dyes can be used for detection of different types of amplified nucleic acids.

A label is any atom or molecule that is used to provide a detectable and/or quantifiable signal. A label can be attached, directly or indirectly, to a polynucleotide or other suitable molecule. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates. A fluorescent dye is any dye that emits electromagnetic radiation of longer wavelength by a fluorescent mechanism upon irradiation by a source of electromagnetic radiation, such as a lamp, a photodiode, or a laser.

Master Mix

A master mix comprises one or more polymerases (e.g., DNA polymerase, reverse transcriptase, and molecules with DNA polymerase and reverse transcriptase activity) and nucleotides and can also contain a PCR buffer. A master mix can be specific for both DNA and RNA polynucleotide sequences. A master mix can be a universal component of assay kits of the invention. That is, a master mix can be used with every assay specific target polynucleotide detection mix.

The master mix can contain a passive fluorescent reference dye. The passive fluorescent dye does not participate in the PCR reaction or in the detection of reaction product. Its emission spectrum is distinguishable from the emission spectrum of all other fluorescent labels used in the PCR reaction. For example, such a passive dye is ROX Reference Dye. The use of a passive fluorescent reference dye allows for normalization to compensate for variations in fluorescence between wells.

DNA Master Mix

A DNA master mix contains one or more DNA polymerases (i.e., DNA-dependent DNA polymerase), dNTP mixture, and one or more PCR buffers. A DNA master mix contains one or more thermostable DNA polymerases suitable for PCR reactions, for example, Taq DNA polymerase, which can be a native enzyme purified from *Thermus aquaticus* and/or a genetically engineered or chemically modified form of the enzyme, e.g., AMPLITAQ or FAST START, or an enzyme transiently inactivated by a ligand, aptamer or antibody, e.g., APTATAQ. Other suitable polymerase enzymes can be used, including those from, e.g., *Thermus thermophilus*. Concentration ranges of the one or more polymerases can range from about 0.5 to about 5.0 units per 100 µl of reaction mixture.

A dNTP mixture comprises deoxyribonucleotide triphosphates of dATP, dCTP, dGTP and dTTP. Optionally, a dNTP mixture may comprise dUTP, either in addition to dTTP, or in lieu of dTTP. In one embodiment, dGTP can be substituted with 7-deaza-2'-deoxy GTP and 7-deaza-2'-deoxy ATP can be substituted for dATP. Additionally, 2'-deoxy ITP can be substituted for any dNTP. The four dinucleotides can be present in a PCR reaction mixture at a concentration of about 20 to about 200 µM and at a pH of about 6.0 to about 8.0, for example about 7.0.

One or more buffers can be part of the DNA master mix. The one or more polymerases, dNTP mixture, and buffers may be present as 2 or 3 different individual components to be mixed at the time of the assay or can be present in one mixture. The buffer can be suitable biological buffer such as Tris-HCl or Tricine, which provide a pH in the range of about 7.4 to about 8.8. The concentration of buffer can be about 10 to about 50 mM for Tris-HCl and about 250 to about 350 mM for Tricine.

The buffer may also comprise a source of magnesium such as $MgCl_2$ or free $Mg^{2+}$. The buffer can contain about 0.5 to about 7.0 mM $Mg^{2+}$. A buffer may also contain, for example, KCl at about 5 to about 50 mM to facilitate primer annealing. β-mercaptoethanol at about 10, 20, 30, 40, or 50 mM, and gelatin or bovine serum albumin (BSA) in a concentration range of 0.01-0.1% can also be present in the buffer. Nonionic detergents such as TWEEN® (polysorbate) 20, Triton X-100, or Laureth 12 in a concentration range of about 0.03 to about 0.1% may also be present in a buffer to stabilize the enzymes.

RNA Master Mix

A RNA master mix contains one or more reverse transcriptases (i.e., RNA-dependent DNA polymerase) (e.g., avian myeloblastosis virus reverse transcriptase; MMLV reverse transcriptase) and one or more thermostable DNA polymerases for subsequent cDNA amplification. Both the reverse transcriptase and DNA polymerase activities may be present in a single enzyme, e.g., HawkZO5. The RNA master mix also comprises a dNTP mixture as described above. The RNA master mix can also comprise one or more buffers. The one or more reverse transcriptases, polymerases, dNTP mixture, and buffers may be present as 2, 3, or 4 different individual components to be mixed at the time of the assay or can be present in one mixture. The one or more buffers can be the same as for the DNA master mix or they may be different. The buffer must support both the reverse transcriptase and DNA polymerase activities and must be compatible with all other components of the system. The RNA master mix can also comprise for example, Mg2+, Mn2+, KCl, RNase H, RNase inhibitors, and/or RNase-free water.

Combined DNA and RNA Master Mix

In one embodiment of the invention, a single master mix can be used for assays wherein either RNA or DNA, or both RNA and DNA are to be detected. The combined DNA and RNA master mix comprises one or more thermostable DNA polymerases, dNTPs, one or more buffers, and one or more thermostable reverse transcriptases. Both the reverse transcriptase and DNA polymerase activities may be present in a single enzyme, e.g., Hawk ZO5. Additionally, the combined DNA and RNA master mix can comprise any of the additional components discussed for the RNA master mix and DNA master mix. The use of a single combined DNA and RNA master mix simplifies handling and work flow and reduces the number of solutions supplied in a kit. One advantage of such simplification is a reduction in the likelihood of user error.

Pooled Positive Control (PPC)

A pooled positive control contains target polynucleotide controls for all DNA and/or RNA target assays. A pooled target positive control can be a universal component of assay kits of the invention. That is, a pooled target positive control can be used with every assay specific detection mix.

In one embodiment of the invention the pooled target positive control contains a target positive control polynucleotide for every polynucleotide target that could possibly be tested for using a kit of the invention.

In another embodiment of the invention, the PPC optionally contains a signature sequence contamination tracer.

In a further embodiment the signature sequence is combined with a single target positive control (PC) polynucleotide, or with 2, 3, 4, 5, 6, 10, 20, 30, 40, 50, 60, 70, 80, 90, 100, 200 or more target positive control polynucleotides.

A pooled target positive control can therefore comprise 2, 3, 4, 5, 6, 10, 20, 30, 40, 50, 60, 70, 80, 90, 100, 200 or more target positive control polynucleotides. A target positive control polynucleotide is a single target positive control polynucleotide. A target positive control polynucleotide comprises a portion of a polynucleotide target sequence (e.g., an organism, gene, or polynucleotide that is to be detected in a test sample) that will be amplified with specific primers such that the amplified amplicons are detectable with one or more probes.

In one embodiment a target positive control polynucleotide is a portion of a naturally occurring nucleic acid (e.g., a portion of a genome of a virus, bacteria or eukaryote). A target positive control polynucleotide comprises a forward primer binding region, a probe binding region and a reverse primer binding region. A target positive control polynucleotide can be about 20, 30, 40, 50, 60, 70, 80, 90, 100, 125, 150, 175, 200, 250, 300 or more nucleic acids in length. A target positive control polynucleotide can be about 300, 250, 200, 175, 150, 125, 100, 90, 80, 70, 60, 50, 40, 30, 20, or less nucleic acids in length.

For example, a target positive control polynucleotide for BVDV will be amplified when using an assay specific target polynucleotide detection mix comprising one or more forward primers and one or more reverse primers specific for BVDV and one or more probes specific for BVDV. The BVDV target positive control polynucleotide is present alone or in a pooled target positive control (comprising about 2 to about 200 or more different target positive control nucleotides). The BVDV target positive control polynucleotide is the only target positive control polynucleotide that will be amplified when a BVDV detection mix is used. The BVDV target positive control polynucleotide will not be amplified when a detection mix for other organisms, genes, or polynucleotides is used.

Pooled target positive control polynucleotides can be designed by the techniques described above for primers and probes. Additionally, such polynucleotides are known in the art for many organisms or genes.

Examples of targets from which target positive control polynucleotides can be designed include, for example, *Actinobacillus pleuropneumoniae* (APP), *Actinobacillus seminis*, *Anaplasma* spp., *Anaplasma phagocytophilum*, Avian Encephalomyelitis (AE), Avian Influenza (AI), Avian Leukosis Virus, Avian Pneumovirus (APV), Avian Reovirus (REO), *Anaplasma platys*, *Babesia* spp., *Babesia canis canis*, *Babesia canis rossi*, *Babesia canis vogeli*, *Babesia conradae*, *Babesia felis*, *Babesia gibsoni*, *Bartonella* spp., *Bartonella henselae*, *Blastomyces dermatitidis*, Blue tongue virus, *Bordetella bronchiseptica*, *Borrelia burgdorferi*, *Borrelia afzelii*, *Borrelia garinii*, Bovine Herpes Virus 1, Bovine Leukemia Virus (BLV), Bovine Viral Diarrhea Virus (BVDV), *Brucella abortus*, *Brucella canis*, *Brucella melitensis*, *Brucella ovis*, BVDV, Caprine Retrovirus, *Calicivirus* spp., *Campylobacter* spp., *Campylobacter coli*, *Campylobacter jejuni*, *Candidatus Mycoplasma haematoparvum*, *Candidatus Mycoplasma* haemominutum, *Candidatus Mycoplasma turicenisis*, Canine Adenovirus 1, Canine Adenovirus 2, Canine *Coronavirus* spp., Canine Distemper Virus (CDV), Canine Hemotropic *mycoplasma*, Canine influenza (H3N8), Canine Parvovirus, canine parvovirus 2 (CPV-2), canine enteric *coronavirus* (CECoV), Canine heartworm, Canine Herpesvirus 1, Canine Herpesvirus spp., Canine Parainfluenza Virus, Canine respiratory *coronavirus* (CRCoV), Caprine Retrovirus (CAE), caprine arthritis encephalitis virus (CAEV), *Chlamydia* spp., *Chlamydophila abortus*, *Chlamydophila felis*, *Circovirus* spp., Classical Swine Fever Virus (CSFV), *Clostridium botulinum*, *Clostridium difficile*, *Clostridium difficile* Toxin A, *Clostridium difficile* Toxin B, *Clostridium perfringens*, *Clostridium perfringens* enterotoxin (CPE and CPEA), *Coccidioides* spp., Contagious Bovine Pleuropneumonia (CBPP), *Coronavirus* spp., *Cryptococcus* spp., *Cryptosporidium* spp., *Cytauxzoon felis*, *Ehrlichia canis*, *Ehrlichia chaffeensis*, *Ehrlichia ewingii*, *Ehdichia* spp., *Encephalitozoon cuniculi*, Enzootic Bovine Leukosis Virus, Ephemeral Fever (3 day sickness)(Ephemerovirus virus), Epizootic Haemorrhagic Disease (EHD), Equine Herpes Virus spp., Equine Herpes Virus 1, Equine Herpes Virus 4, Equine Infectious Anemia, Equine influenza virus A, Equine Viral Arteritis (EVA), *Fasciola hepatica*, Feline *Calicivirus* spp., Feline Herpesvirus spp., Feline herpesvirus Type 1, Feline *Coronavirus* (FCoV), Feline Haemotropic *Mycoplasma*, Feline Heartworm, Feline Herpesvirus spp., Feline *Calicivirus* spp., feline panleukopenia virus, Feline Parvovirus spp., Feline Immunodeficiency Virus (FIV) Types A, B, C, D, E, and F, Feline Leukemia Virus, Foot-and-Mouth Disease (FMD), *Giardia* spp., H1N1 Influenza virus, Hantaan Virus, hepatitis A, hepatitis B, hepatitis C, *Hepatozoon* spp., *Hepatozoon americanum*, *Hepatozoon canis*, *Histoplasma capsulatum*, *Hypoderma* spp., Infectious Bursal Disease (infectious bursal disease virus (IBDV)), Japanese Encephalitis, Equine Arteritis Virus, Equine *coronavirus*, Equine Herpesvirus Type 1 and 4, Equine Infectious Anemia, Equine Influenza Virus, Equine Protozoal Myeloencephalitis, Equine rotavirus, Johne's Disease (*Mycobacterium avium* subspecies *paratuberculosis*), Knotts Testsee Microfilaria, Kunjin Virus, *Lawsonia intracellularis*, *Leishmania* spp., *Leptospira* spp., *Fasciola hepatica*, Maedi-visna virus (MW), Masticatory Myositis, Melioidosis (*Burkholderia pseudomallei*), *Mycobacterium* spp., *Mycoplasma meleagridis Mycobacterium avium* subsp. *paratuberculosis, Mycobacterium bovis, Mycoplasma* spp., *Mycoplasma agalactiae, Mycoplasma cynos, Mycoplasma felis, Mycoplasma gallisepticum, Mycoplasma haemofelis, Mycoplasma haemocanis, Mycoplasma hyopneumoniae, Mycoplasma ovis, Mycoplasma bovis, Mycoplasma synoviae, Neorickettsia risticii, Neospora* spp., *Neospora caninum*, Newcastle Disease, Nipah Virus, Ophidian Paramyxovirus, porcine parvovirus, Porcine Reproductive and Respiratory Syndrome (PRRS), Pestivirus spp., Pseudorabies virus, Q Fever (*Coxiella burnetti*), Rabbit *calicivirus* spp., *Rhodococcus equi*, Rocky Mountain Spotted Fever (*Rickettsia rickettsia*), Ross River Virus, Rotavirus *Sarcocystis neurona*, Schmallenberg Virus (SBV), Scours, Rotavirus spp., *Salmonella* spp., *Salmonella enteritidis* (SE), Simbu virus, *Streptococcus equi* subsp. *equi* (Strangles), *Streptococcus equi* subsp. *zooepidemicus*, Swine Influenza Virus (SIV), *Taylorella equigenitalis, Toxoplasma gondi, Trichinella* spp., *Tritrichomonas foetus*, West Nile virus, parasites, helminths, hookworm, roundworm, whipworm, tapeworm, heartworm, lungworm. Targets from which target positive control polynucleotides can be designed further include disease related nucleic acids of a vertebrate, mammalian, avian animal, or a human, such as genetic alleles, nucleic acid markers, genes and RNA transcripts associated with medical conditions or resistance thereto. Any combination of target control polynucleotides can be pooled from this list or from targets known in the art.

The number of pooled target positive control polynucleotides or target positive control polynucleotides in the assay should be near the lower limit of detection for the assay, yet is at a high enough number to provide consistent positive results. The number of target positive control polynucleotides can be about 1, 5, 10, 15, 20, 30, 40, 50, 60, 70, 80, 90, 100, 200, 500, 1,000, 2,500, 5,000, 10,000 (or any range between about 1 and 10,000) or more. The number of target positive control polynucleotides can be about 10,000, 5,000, 2,500, 1,000, 500, 200, 100, 90, 80, 70, 60, 50, 40, 30, 20, 15, 10, 5 (or any range between about 10,000 and 1) or less. Examples of ranges of numbers of target positive control polynucleotides include about 10 to about 50; about 50 to about 500; about 10 to about 100; and about 10 to about 1,000.

Forward primers, reverse primers and probes for an assay specific target polynucleotide detection mix can also be designed individually for each of these targets.

The signature sequence is a tracer for contamination with a single positive control (PC) or with a PPC. The signature sequence polynucleotide is a random, artificial or natural polynucleotide. The signature sequence polynucleotide does not cross-amplify with any of the other polynucleotides or controls in the assay system. One example of a signature sequence is shown in FIG. 4. The signature sequence polynucleotide can be present at an equal or higher molar concentration than one or more of the target positive control polynucleotides in the PPC. For example, the molar concentration of the signature sequence polynucleotide can be 1, 2, 3, 4, 5, 6, 7, 8, 9, 10, 15, 20, 50, 75, or 100-fold or more higher than the molar concentration of one or more of the target positive control polynucleotides. A higher molar concentration can be used to ensure that the amplification and detection of the signature sequence polynucleotide is more sensitive than the detection of the target positive control polynucleotides. Thus, the likelihood of detection of a contamination with PPC is maximized.

The signature sequence polynucleotide can be used in several ways. First, where cross-contamination with PPC or a single PC is suspected (that is, if it is suspected that the PPC has been introduced into other stock solutions or into the general work environment), a test can be set up to determine if the signature sequence is present and amplifiable. In a second use, a multiplexing of signature sequence could be done with every assay, thus allowing for the detection of any potential contamination with PC or PPC concurrently with the detection of a specific target polynucleotide. In this instance, an additional fluorescent probe color and additional color channel on the PRC machine would be required.

A signature sequence detection mix comprises primers (forward and reverse) and one or more probes that can be used to amplify and detect the signature sequence. Optionally, the signature sequence detection mix can be combined with an assay specific target polynucleotide detection mix.

One embodiment of the invention provides a pooled target positive control composition comprising two or more target positive control polynucleotides for two or more target polynucleotides and one or more signature sequence polynucleotides. The composition can comprise 10, 20, 30, 40, 50, 60, 70, 80, 90, 100, 150, 200 or more target positive control polynucleotides for 10, 20, 30, 40, 50, 60, 70, 80, 90, 100, 150, 200 or more target polynucleotides. The two or more target positive control polynucleotides for two or more target polynucleotides can comprise both DNA and RNA target positive control polynucleotides. The one or more target positive control polynucleotides can be minimers (see below).

The invention also provides a method of testing for contamination of a PCR sample comprising loading one or more vessels with: (a) a sample to be tested for contamination; (b) detection mix for a signature sequence; and (c)

master mix comprising one or more polymerases, nucleoside triphosphates, and optionally one or more reverse transcriptases; and subjecting the one or more vessels to polymerase chain reaction conditions.

Internal Sample Control (Sample Integrity Control) (ISC) Detection Mix

An ISC detection mix amplifies and detects conserved regions of eukaryotic RNA or DNA, for example 18S DNA. The ISC primers and probe can be designed to bind to one or more conserved eukaryotic polynucleotides from animals of interest, e.g., bovine, human, avian, equine, feline, canine, or murine animals or combinations thereof. This control is used to confirm integrity of genomic DNA of the patient or subject as well as its successful extraction from the patient or subject sample. This control can be run in a separate tube/well or may be multiplexed and run with every assay specific target polynucleotide assay.

Examples of ISC primers and probes include primers and probes for eukaryotic 18S DNA such as:

```
                                           (SEQ ID NO: 15)
E18S-41f GATTAAGCCATGCATGTCTAAGTACG 59.2

(SEQ ID NO: 16)
E18S-123r CAAAGGAACCATAACTGATTTAATGAGC 60.4

TaqMan probe
                                           (SEQ ID NO: 17)
E18S-67p CACGGCCGGTACAGTGAAACTGCG 70.1.
```

Other primers and probes that are specific for eukaryotic 18S DNA can be used. Additionally, any other forward primers, reverse primers and probes specific for conserved eukaryotic polynucleotides (DNA and corresponding RNA), which are well-known in the art, can be used in the methods of the invention. See Parra et al., Bioinformatics, 23:1061 (2007), which teaches 458 conserved core eukaryotic polynucleotides that can be used in the methods of the invention. See also, Koonin et al., Genome Biol. 5:R7 (2004), which teaches eukaryotic orthologous groups (KOGs) that can be used as conserved eukaryotic polynucleotides in the methods disclosed herein. Both sequences coding for proteins and non-coding sequences can be used as conserved eukaryotic polynucleotides. A conserved eukaryotic polynucleotide is a polynucleotide sequence where similar (more than 95, 96, 97, 98, 99% homology) or identical (100% homology) sequences (RNA and DNA) occur in at least 2, 3, 4, 5, 6, or more species. A conserved eukaryotic polynucleotide can be, e.g., an ultra-conserved eukaryotic polynucleotide (sequences that share 100% identity among human, mouse and rat). See e.g., Bejerano et al., Science, 304(5675): 1321 (2004); Reneker et al. "Long identical multispecies elements in plant and animal genomes" PNAS 109 (19): 1183 (2012).

One of skill in the art can design primers and probes that are specific for conserved eukaryotic polynucleotides. Examples of conserved eukaryotic polynucleotides include housekeeping genes (e.g., GADPH, ACTB, UBC) and repetitive elements. An internal sample control detection mix comprises one or more primers (forward and reverse) and one or more probes that can be used to amplify and detect conserved regions of conserved eukaryotic polynucleotides, such as for example 18S DNA. Optionally, the internal sample control detection mix can be combined with an assay specific target polynucleotide detection mix.

Quality Control Detection Mixes

Assays and kits of the invention can further include additional detection mixes for controls such as an internal positive control, a positive control contamination control (e.g., signature sequence), an environmental contamination control (e.g., PanB), or combinations thereof. Quality control detection mixes are universal components of assay kits of the invention. That is, a quality control detection mix is compatible with the other universal components of the PCR test system, for example the one or more master mixes. One or more of the quality control detection mixes can be combined with any assay specific target polynucleotide detection mix.

Internal Positive Control (IPC)

An internal positive control is one or more pairs of DNA and RNA synthetic non-target polynucleotides that can be used as an extraction and/or an amplification control. An internal positive control can be a universal component of assay kits of the invention. That is, an internal positive control can be used with every assay specific target polynucleotide detection mix. An IPC polynucleotide may be single stranded, or partially double stranded, or entirely double stranded.

A pair of DNA and RNA IPCs share one or two of three sequence elements: (1) a forward primer binding region; (2) a probe binding region; and (3) a reverse primer binding region. See FIGS. 1A, 2. That is, a DNA IPC can comprise a forward primer region that is the same or similar to the RNA IPC (e.g., forward primer 1, but a different probe and reverse primer region such as probe region 1 and reverse primer region 3 for the DNA IPC, while the RNA IPC has probe region 2 and reverse primer region 3). The DNA IPC and RNA IPC have one or two sequence elements that are different from each other. Note that the RNA IPC is made up of ribonucleic acids while the DNA IPC is made up of deoxyribonucleic acids. Therefore, where a region is the "same" between a DNA IPC and a RNA IPC, the DNA IPC contains a thymine at one position, but the RNA contains a uracil at that position. The regions are considered the "same" even though the RNA IPC has a uracil at a position and the DNA IPC contains a thymine at the corresponding position. See, e.g., FIG. 1A, where the reverse primer binding site and probe binding sites are the "same."

Same means 100% homology wherein a thymine in DNA is considered complementary to uracil in RNA. Similar means the DNA and RNA IPC regions have about 70, 75, 80, 85, 90, 91, 92, 93, 94, 95, 96, 97, 98, 99% or more homology between the regions, where thymine in DNA is considered 100% homologous to uracil in RNA. Different primer binding regions or probe binding regions comprise less than about 60, 50, 40, 30, 20, or 10% homology between two regions.

The one or two different forward primer binding regions, reverse primer binding regions, and probe binding regions combined with one or two same or similar forward primer binding regions, reverse primer binding regions, and probe binding regions between the DNA IPC and the RNA IPC allow for the differentiation of amplification of the RNA IPC or the DNA IPC.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

One of skill in the art can design a "sequence toolbox" of forward primer binding regions, probe binding regions, and reverse primer binding regions. See FIG. 2. The sharing of same or similar primer and probe binding regions between DNA IPCs and RNA IPCs increases manufacturing efficiency.

The sequence of the forward primer binding region, the reverse primer binding region, and the probe binding region can be determined by any method known to those of skill in the art for determining a random sequence of four possibilities (A, T, G, and C). Examples of such methods, include but are not limited to, use of computer software designed to produce random nucleotide sequences.

The internal positive control sequence should have no significant nucleotide identity to any known, naturally occurring nucleotide sequences, which means that the sequence of base pairs of the forward primer binding site and the reverse primer binding site are designed such that they should not hybridize to naturally-occurring nucleotide sequences in a PCR-amplifiable region of the genome of a single organism. Thus, the forward and reverse primers should in combination not typically be capable of amplification of a naturally-occurring sequence at the hybridization temperatures and polymerase extension times typically used in PCR, such as real-time PCR.

The primers and probes used with the internal positive control polynucleotide can be designed with characteristics specific to certain types of PCR assays and can be designed using computer software such as Primer Express. Examples of these characteristics include, but are not limited to amplicon size and primer melting temperature. The primers and probes are designed to be compatible during amplification without the formation of primer dimers.

An RNA IPC can be manufactured in two ways. First, an RNA IPC can be made using by chemical synthesis. Alternatively, an RNA IPC can be made by first making a DNA template that incorporates a promoter (such as a T7 promoter), then transcribing this DNA template in vitro with RNA polymerase to make the desired RNA IPC. The DNA template can be double stranded (dsDNA) in at least the promoter region. The promoter occurs at the 5' end (upstream of the forward primer region) of the DNA template for making the RNA IPC.

A number of promoters may be used for the promoter region. The promoter region can comprise between about 15 and about 250 nucleotides, for example, between about 17 and about 35 nucleotides, from a naturally occurring promoter, a consensus promoter region, or an artificial promoter region. See e.g., Alberts et al. (1989) in Molecular Biology of the Cell, 2d ed. (Garland Publishing, Inc.). Prokaryotic promoters, eukaryotic promoters, phage or virus promoters can be used. Representative promoter regions include, for example, T7, T3 and SP6. See e.g., Chamberlin and Ryan, The Enzymes (ed. P. Boyer, Academic Press, New York) (1982) pp 87-108. The promoter sequence can be, for example, T7 promoter sequence comprising at least nucleotides −17 to +6 of a wild-type T7 promoter sequence, joined to about 10, 20, or 30 nucleotides of upstream flanking sequence, particularly upstream T7 promoter flanking sequence. Additional downstream flanking sequence, particularly downstream T7 promoter flanking sequence, e.g. nucleotides +7 to +10, may also be used. For example, the promoter can comprise nucleotides −50 to +10 of a T7 promoter sequence. A T7 promoter can comprise 5'-TAATACGACTCACTATAGGG-3' (SEQ ID NO:10). In some embodiments, an IPC comprises an intervening spacer sequence between the optional promoter region, the forward primer binding region, the probe binding region, the reverse primer binding region or combinations thereof. Suitable lengths of the intervening spacer sequences can be about 1, 2, 3, 4, 5, 6, 7, 8, 9, 10, 12, 15, 20, 30 40, 50, 60, 70, 80, 90, 100, 150, 200, 250, 300, 400, 500 or more nucleic acid bases. intervening spacer sequences can also be about 500, 400, 300, 250, 200, 150, 100, 90, 80, 70, 60, 50, 40, 30, 20, 15, 12, 10, 9, 8, 7, 6, 5, 4, 3 or fewer nucleic acid bases. Spacer sequences can be designed to not interfere with amplification or to enhance the degree of amplification as compared to omission of the spacer sequence. The spacer sequences are not homologous (i.e., they do not substantially hybridize) to the target nucleic acids.

The length of each of the forward primer binding region, the reverse primer binding region and the probe binding region can be about 5, 10, 15, 20, 25, 30, 35, 40, 50, 60, 65, 70, 75, 80, 85, 90 or more nucleotides. These regions can also be about 90, 85, 80, 75, 70, 65, 60, 50, 40, 35, 30, 25, 20, 15, 10, 5 or fewer nucleotides. The length of each region can be about 10 to about 50, or about 15 to about 30, or about 20 to about 30 nucleotides. The length of an entire IPC can be about 30, 40, 50, 60, 70, 80, 90, 95, 100, 110, 120, 130, 140, 150, 160, 170, 180, 190, 200, 210, 215, 220, 230, 240, 250, 300, 400, 500, or more nucleotides. An entire IPC can also be about 500, 400, 300, 250, 240, 230, 220, 215, 210, 200, 190, 180, 170, 160, 150, 140, 130, 120, 110, 100, 95, 90, 80, 70, 60, 50, 40, 30 or less nucleotides. The length of an entire IPC can be about 50 to about 100, from about 60 to about 90, about 70 to about 80, from about 100 to about 200, or from about 150 to 250 nucleotides. The complementarity of the hybridizing portion of the forward primer binding region to the forward primer, the hybridizing portion of the probe binding region to the probe, and the hybridization portion of the reverse primer binding region to the reverse primer at least about 75%, 80%, 85%, 90%, 95%, 96%, 97%, 98%, 99% or 100%.

An IPC detection mix contains primers (forward and reverse) and probe specific for either one or more DNA IPCs or one or more RNA IPCs, depending on whether the specific assay is an RNA test (e.g., a test for a retrovirus) or a DNA test (e.g. a test for bacterial DNA). For example, a detection mix can comprise a forward primer that binds to the forward primer binding region of the IPC, a probe that binds to the probe binding region of the IPC, a reverse primer that binds to the reverse primer binding region of the IPC. Optionally, an IPC detection mix contains primers (forward and reverse) and probes for one or more DNA IPCs and one or more RNA IPCs. The IPC primers and probes are present in a buffer, and optionally, in an RNase safe buffer.

The primers and probes in a pair of DNA and RNA IPC detection mixes correspond to a DNA and RNA IPC pair. Thus, a pair of DNA and RNA IPC detection mixes share one or two of the following three polynucleotides: (1) a forward primer (2) a probe; and (3) a reverse primer. See FIGS. 1A, 2. That is, a DNA IPC detection mix can comprise a forward primer that is the same or similar to the RNA IPC (e.g., forward primer 1, but a different probe and reverse primer such as probe 1 and reverse primer 3 for the DNA IPC, while the RNA IPC has probe 2 and reverse primer 3). The DNA IPC and RNA IPC detection mixes have one or two polynucleotides that are different from each other.

One or more IPC detection mixes can be combined with one or more assay specific detection mixes. For example, a combined detection mix can comprise a forward primer that binds to the forward primer binding region of the IPC, a probe that binds to the probe binding region of the IPC, a reverse primer that binds to the reverse primer binding region IPC, a forward primer that binds to the forward primer binding region of the specific assay polynucleotide target, a probe that binds to the probe binding region of the specific assay polynucleotide target, a reverse primer that binds to the reverse primer binding region of the specific assay polynucleotide target.

All polynucleotides described above and throughout this specification can be prepared using any suitable method, such as, for example, the known phosphotriester and phosphite triester methods, or automated embodiments thereof. Polynucleotides can be synthesized by a number of approaches, e.g. Ozaki et al., Nucleic Acids Research, 20:5205-5214 (1992); Agarwal et al., Nucleic Acids Research, 18:5419-5423 (1990). The polynucleotides of the invention can be synthesized on an automated DNA synthesizer using standard chemistries, such as phosphoramidite chemistry, e.g. disclosed in the following references: Beaucage & Iyer, Tetrahedron, 48:2223-2311 (1992); Molko et al., U.S. Pat. No. 4,980,460; Koster et al, U.S. Pat. No. 4,725,677; Caruthers et al., U.S. Pat. Nos. 4,415,732; 4,458, 066; and U.S. Pat. No. 4,973,679. Alternative chemistries, e.g. resulting in non-natural backbone groups, such as phosphorothioate, phosphoramidate, and the like, can also be employed provided that the hybridization efficiencies of the resulting oligonucleotides and/or cleavage efficiency of the exonuclease employed are not adversely affected.

The IPC forward primer region, probe region, and reverse primer region are synthetic DNA and RNA sequences that are not in total found in nature (the individual elements may occur in nature, but not the combinations/arrangements in which they occur in the IPCs). The DNA IPC can be added to DNA only tests, and the RNA IPC can be added to RNA only tests. The DNA IPC and RNA IPC can be combined in a RNA-safe buffer for use in either DNA or RNA tests, or for combined RNA and DNA tests. The use of a pair of DNA and RNA IPCs that share primer and probe sequences between DNA and RNA increases manufacturing efficiency while being able to control for both RNA and DNA assays, including the reverse transcription step and the extraction/purification steps. The combination of DNA and RNA IPCs in a single tube/well reduces the number of kit components, simplifies work flow and inventory for the user, and reduces the chance of user error.

To run an assay with an IPC, the template and primers for the internal positive control are included in the reaction along with those for the polynucleotide target of interest. The amplification of the IPC can be distinguished (using, for example, separate detection probes with different fluorescent dye colors) from the amplification of the target of interest. The use of IPCs advantageously does not require a separate reaction and is useful because they can identify problems that are intrinsic to the sample reaction. For example, IPCs can detect a situation where substances in the clinical sample inhibit the PCR reaction, or a situation where the nucleic acids were not properly extracted and/or recovered. For example, sputum and stool samples often contain inhibitory substances that may not be removed by the extraction process. IPCs can be added to the test sample prior to the nucleic acid extraction (e.g., to the lysis buffer) or can be added to the PCR reagent mix prior to nucleic acid amplification.

Where both the target nucleic acids and an internal positive control do not amplify, then PCR inhibition or extraction failure is assumed and the assay test result is disregarded. If target is amplified and internal control is not amplified then it is concluded that the target nucleic acids are present in a much greater concentration than the internal control nucleic acids. This positive result can be considered valid, provided that all negative controls have the expected negative result. If the target is not amplified and the internal control and/or internal positive control is amplified, then it is concluded that the test is valid and negative for the target.

Minimers

Positive controls for PCR reactions are essential for confirmation of the proper activity of multiple reaction components. For example, using a positive control in the form of synthetic RNA in an RT-PCR reaction ensures proper reverse transcriptase activity, as well as the proper functioning of the primers and probes of the RT-PCR reaction. Among the benefits of using synthetic DNA and/or RNA as positive controls are their purity and reliable quantification. However, current techniques for synthesizing nucleic acids have size limitations. For example, the length of synthetic RNA oligomers is currently limited to about 70-90 bases, depending on the methodology. In addition, synthesis costs increase with increasing oligomer length.

A novel method for adapting the size of target amplicons has been developed. The method can be used to limit the length of an RNA or DNA molecule to be used as a positive control, to less than about 100, less than about 90, less than about 75, or less than about 60 bases. This results in lower cost and/or easier manufacturability. A positive control can be an internal positive control or a target positive control or an internal sample control and can be DNA or RNA.

The summary of the adaptation is shown in FIG. 5. Briefly, some or all of the intervening sequences between the primer and probe binding sites of the naturally occurring sequence are removed, creating a mini-amplicon, herein also referred to as a "minimer" that will retain all of the useful properties of a full-length control. A minimer comprises a forward primer binding region, a probe binding region and reverse primer binding region. The length of each of the forward primer binding region, the reverse primer binding region and the probe binding region can be about 5, 10, 15, 20, 25, 30, 35, 40, 50, 60, 65, 70, 75, 80, 85, 90 or more nucleotides. These regions can also be about 90, 85, 80, 75, 70, 65, 60, 50, 40, 35, 30, 25, 20, 15, 10, 5 or fewer nucleotides. The length of each region can be about 10 to about 50, or about 15 to about 30, or about 20 to about 30 nucleotides. In one embodiment, additional sequence of about 1, 2, 3, 4, 5, 6, 7, 8, 9, 10, 11, 12, 13, 14, 15 or more bases in length are added to the ends of the mini-amplicon to allow for slight degradation of a DNA or RNA molecule without an adverse effect on primer binding. For example, between about 5 and 15 nucleic acid bases 5' to the forward primer binding site and between about 5 and 15 nucleic acid bases 3' to the reverse primer binding site that have homology (e.g., about 75, 80, 85, 90, 95, 96, 97, 98, 99, 100% homology) to the target polynucleotide.

The length of an entire minimer can be about 30, 40, 50, 60, 70, 80, 90, 95, 100, 110, 120, 130, 140, 150 or more nucleotides. An entire minimer can also be about 150, 140, 130, 120, 110, 100, 95, 90, 80, 70, 60, 50, 40, 30 or less nucleotides. The length of an entire minimer can be about 50 to about 100, from about 60 to about 90, about 70 to about 80, from about 100 to about 150, or from about 125 to 150 nucleotides.

Therefore, a minimer polymerase chain reaction control ribonucleic acid molecule or deoxyribonucleic acid molecule can comprise a forward primer binding region, a probe binding region, and a reverse primer binding region. Each of the primer binding region, the probe binding region, and the reverse primer binding region have homology to a corresponding forward primer binding region, a probe binding region and a reverse primer binding region in a target polynucleotide. The target polynucleotide can be a portion of a naturally occurring DNA or RNA polynucleotide. The homology can be about 100% or 75, 80, 85, 95, 96, 97, 98, 99 or more. The minimer has fewer nucleic acid bases than a region of the target polynucleotide (which can be a portion of naturally occurring DNA or RNA polynucleotide) comprising the forward primer binding region, the probe binding region, the reverse primer binding region and any intervening regions for which the polymerase chain reaction control ribonucleic acid molecule serves as a control. For example about 5, 8, 10, 20, 30, 40, 50, 60, 70, 80, 90, 100, 150, 200, 250, 300, 400, 500 or more fewer nucleic acid bases.

The minimer can have fewer nucleic acid bases between the forward primer binding region and the probe binding region than occurs in the target polynucleotide and can have fewer nucleic acid bases between the probe primer binding region and the reverse binding region than occurs in the target polynucleotide. For example about 1, 2, 3, 4, 5, 6, 7, 8, 9, 10, 20, 30, 40, 50, 60, 70, 80, 90, 100 or more fewer nucleic acid bases in each of those regions. Therefore, a minimer is a non-naturally occurring polynucleotide.

Positive Control Contamination Control.

The positive control contamination control is the detection mix for the signature sequence. Contamination with one or more positive control polynucleotides can be traced by amplification of the signature sequence. This assay can be run as an individual test or it can be multiplexed and run with every assay specific target polynucleotide assay.

A positive control contamination detection mix comprises primers (forward and reverse) and one or more probes that can be used to amplify and detect the signature sequence. Optionally, the positive control contamination control detection mix can be combined with an assay specific target polynucleotide detection mix.

PanB Detection Mix (Environmental Testing)

This control is used as a positive control when performing routine environmental contamination monitoring as this detection mix is able to amplify and signal the presence of highly conserved bacterial DNA sequences present in many environmental bacteria, such as 16S ribosomal DNA. Windsor et al., J Vet Intern Med. 20(2):250-6 (2006). This control can detect a prokaryote's DNA where there is a contaminating prokaryote present.

For example, this control may amplify prokaryotic 16S DNA ribosomal DNA (test for environmental contamination or as internal sample control for fecal samples).

Examples of PanB primers and a probe include:

```
                                          (SEQ ID NO: 18)
PanB.283f GGATGATCAGCCACACTGGA (SEQ ID NO: 19)
PanB.352r CCAATATTCCTCACTGCTGCC (SEQ ID NO: 20)
PanB.305p CCCGTAGGAGTCTGGACCGTGTCTCA
```

Other primers and probes specific for conserved bacterial 16S ribosomal DNA regions can be used. Furthermore, primers and probes specific for highly conserved bacterial 23S ribosomal DNA regions, tRNA genes, or ABC Transporter Binding Domain genes can be suitable as controls for environmental contamination monitoring. Isenbarger et al., Orig Life Evol Biosph. 38(6):517-33 (2008). This assay can be run as an individual test or it can be multiplexed and run with every assay specific target polynucleotide assay. For a fecal patient sample, the PanB test may also be used as an Internal Positive Control due to the presence of bacterial nucleic acids in feces.

A PanB detection mix comprises one or more primers (forward and reverse) and one or more probes that can be used to amplify and detect one or more conserved prokaryotic polynucleotides, such as 16S rDNA. See Segarth and Huttenhower, PLoS One 6:e247094 (2011), which discloses a list of conserved prokaryotic polynucleotides. Both sequences coding for proteins and non-coding sequences can be used as conserved prokaryotic polynucleotides. A conserved prokaryotic polynucleotide is a polynucleotide sequence where similar (more than 95, 96, 97, 98, 99% homology) or identical (100% homology) sequences (RNA and DNA) in at least 2, 3, 4, 5, 6, 7, 8, 9, 10 or more prokaryotic species. A conserved prokaryotic polynucleotide can also be a polynucleotide sequence where similar (more than 95, 96, 97, 98, 99% homology) or identical (100% homology) sequences (RNA and DNA) occur in at least 2, 3, 4, 5, 6, 7, 8, 9, 10 or more prokaryotic genera. A conserved prokaryotic polynucleotide can encode e.g., one or more of a cluster of orthologous group of proteins (COGs) (see Tatusov et al., BMC Bioinformatics. 2003 September 11; 4) or one or more of eggNOGs (see Jensen et al. eggNOG: automated construction and annotation of orthologous groups of genes. Nucleic Acids Res. 2008; 36:D250-D254). One of skill in the art can design and make forward primers, reverse primers, and probes specific for conserved prokaryotic polynucleotides. Optionally, the Pan B detection mix can be combined with an assay specific target polynucleotide detection mix.

Compositions

One embodiment provides a mixture of nucleic acid amplification reagents comprising:
(a) a master mix comprising one or more DNA polymerases, nucleoside triphosphates, and optionally one or more reverse transcriptases;
(b) a pooled target positive control comprising two or more target positive control polynucleotides for two or more target polynucleotides and one or more signature sequence polynucleotides; and
(c) an internal sample control detection mix comprising one or more forward primers, one or more reverse primers, and one or more probes that can amplify and detect one or more conserved eukaryotic polynucleotides;

wherein each of (a), (b), and (c) are each individual mixtures; or wherein one or more of (a), (b), and (c) are combined together into one or more mixtures; or wherein (a), (b), and (c) are combined together in a single mixture.

In an alternative embodiment, component (b) (i.e., the pooled target positive control) can be removed and component (b) can replaced with an assay specific target polynucleotide detection mix comprising one or more assay specific forward primers, one or more assay specific reverse primers, and one or more assay specific probes.

Referring to both embodiments above, the one or more DNA polymerases can be combined reverse transcriptase PCR DNA polymerases. The mixture can further comprise an assay specific target polynucleotide detection mix comprising one or more assay specific forward primers, one or more assay specific reverse primers, and one or more assay specific probes, wherein the assay specific target polynucleotide detection mix is an individual mixture or is combined with one or more of (a), (b) or (c). The pooled target positive control comprises 10, 20, 30 or more target positive control polynucleotides for 10, 20, 30 or more target polynucleotides.

The mixtures above can further comprise a quality control detection mix comprising one or more of:
  (a) an internal positive control polynucleotide pair comprising a DNA internal positive control (IPC) polynucleotide and a RNA internal positive control (IPC) polynucleotide, wherein the DNA IPC and the RNA IPC share one or two same or similar forward primer binding regions, probe binding regions, or reverse primer binding regions, and wherein one or two of the forward primer binding regions, probe binding regions, or reverse primer binding regions of the DNA IPC and the RNA IPC are different;
  (b) a signature sequence; and
  (c) PanB detection mix comprising one or more forward primers, one or more reverse primers and one or more probes that can amplify and detect one or more conserved prokaryotic polynucleotides.

The assay specific target polynucleotide detection mix further can comprise one or more internal positive control forward primers, one or more internal positive control reverse primers, and one or more internal positive control probes. The master mix, pooled target positive control, and internal sample control detection mix can be universal components that can be used with any assay specific target polynucleotide detection mix. The assay specific target polynucleotide detection mix can comprises assay specific reverse primers, assay specific forward primers, and one or more assay specific probes for two or more different target polynucleotides. The two or more different target polynucleotides can comprise RNA polynucleotides and DNA polynucleotides. The master mix, pooled target positive control and internal sample control detection mix can be used to amplify both DNA polynucleotide targets and RNA polynucleotide targets on the same multiwell device.

Thus, through the methods of the invention, both RNA and DNA polynucleotides can be amplified using a single master mix using an enzyme having DNA-dependent polymerase activity and RNA-dependent DNA polymerase activities (e.g., HawkZ05) or a mixture of one or more DNA polymerases and one or more reverse transcriptases. In addition, both RNA and DNA polynucleotides can be amplified with a single thermocycling program. Therefore, both RNA and DNA polynucleotides can be amplified simultaneously in a single thermocycler. Both RNA and DNA polynucleotides can be amplified in same or separate reaction vessels located on a single multiwell device, such as a microtiter plate, or a device having a multitude of microwells or nanowells.

Modular System

The components of the PCR platform system of the invention can be provided to the user as individual modules, as opposed to complete kits, or as opposed to kits that contain several components (FIG. 3A-B). For example, a Master Mix module can comprise the master mix, but not a detection mix nor a target positive control or ISC detection mix. A Detection Mix module can comprise a mix of least two primers and at least one probe, but not a master mix nor a single target positive control or ISC detection mix. A Detection Mix module may comprise a combination of target specific probe and primers and control specific primers and probes. The PC or PPC module comprises a mix of at least one target positive control template polynucleotide and a signature sequence polynucleotide, but not an ISC detection mix, nor a detection mix, nor a master mix. An optional IPC module can comprise a mix of DNA and RNA IPC, but not a detection mix, nor a master mix or a PPC. One advantage of a modular system is that the user can purchase and inventory each component in the amounts needed for his or her specific purposes. This is advantageous, e.g., for a laboratory that performs a multitude of different target specific test, especially if different tests are carried out at different frequencies and/or in different numbers or volumes. The modular system approach of the invention leads to simplified handling and inventory, and reduced waste, such as waste by expiration of reagent shelf life.

In one embodiment a user buys and uses one or more assay specific detection mixes, RNA and/or DNA master mix, pooled target positive control (optionally with a signature sequence), IPC (optionally with IPC detection mix), and optionally quality control mixes. See FIG. 3A. In other embodiments, a user buys and uses RNA master mix and/or DNA master mix, assay specific detection mix, ISC specific primers and probes, PPC and optionally quality control reagents. See FIG. 3B.

Any component of the invention (e.g., primers, probes, detection mixes, ISCs, buffers, master mixes, PPCs, assay specific target polynucleotide detection mix, test samples, IPCs, IPC detection mix, positive contamination controls, signature sequences, detection mix for signature sequences, PanB detection mix, etc.) can be present separately in a well or mix or storage device or in any combination of two or more components.

Methods

Assays of the invention can be used with any type of sample, for example, blood, serum, plasma, urine, feces, saliva, sputum, semen, lung aspirate, cerebrospinal fluid, throat swab, tracheal swab, nasal swab, vaginal swab, rectal swab, poultry cloaca swab, a biopsy sample, tissue, ear notch, ear punch, cells, tears, nasal secretions, milk, environmental sample, tumor tissue or cells, lymphatic fluid samples, amniotic fluid samples, plant samples, needle aspiration biopsy samples, cell lysate samples, crude cell lysate samples, forensic samples, archeological samples, infection samples, nosocomial infection samples, soil samples, water samples, food samples and combinations thereof. Samples can be obtained from, for example, any type of animal, for example, a mammal, a human, dog, cat, horse, ovine, bovine, porcine, rodent, goat, bird, fish or combinations thereof.

Once the sample is obtained, the nucleic acids can be extracted manually, for example using phenol-chloroform extraction methods or kits such as High Pure (Roche), QIAamp (Qiagen), IsoQuick (Orca research), and IsoCode Stix (Schleichar & Schuell). Nucleic acid extraction can also be achieved with rapid lysis methods, i.e., NukEx (Gerbion), which is based on enzymatic release of nucleic acids from tissues or organisms. Automated extraction techniques can also be used (MagNA Pure (Roche Applied Science), BioRobot (Qiagen), ABI Prism (Applied Biosystems), NucliSens Extractor (bioMérieux). The DNA and/or RNA IPCs can be added prior to nucleic acid extraction. Alternatively, they can be added after nucleic acid extraction.

Universal thermocycling conditions for all diagnostic tests allow the user to run assays for both RNA and DNA polynucleotide targets side-by-side on the same reaction plate. Universal cycling conditions include a sufficient incubation time and temperature to support the reverse transcription step in case of an RNA assay (RT-PCR).

1. A PCR assay can comprise one or more of the following reactions. Each reaction can be in its own vessel (e.g., a well in a multiwell assay plate). Examples of reaction mixtures include, for example: One or more testing wells can contain, for example, a test sample, an ISC detection mix, one or more assay specific target polynucleotide detection mixes specific for target polynucleotides that are to be tested for in the test sample (both here and in all other embodiments, the ISC detection mix can be combined with one or more assay specific target polynucleotide detection mixes, and master mix.
2. One or more positive control wells containing pooled target positive control or single target positive control, signature sequence, one or more assay specific target polynucleotide detection mixes for specific targets, and master mix.
3. One or more negative control wells containing water or buffer, one or more assay specific target polynucleotide detection mixes for the specific polynucleotide assay targets, and master mix
4. One or more IPC wells containing the test sample, a DNA IPC, an RNA IPC, or both DNA and RNA IPCs, detection mix for either the RNA or the DNA IPC or both the RNA and the DNA IPC (dependent on whether the specific assay target is RNA or DNA or both), and master mix.
5. One or more signature sequence wells containing environmental swab or other sample to be tested for contamination, detection mix for the signature sequence, and master mix.
6. One or more PanB detection mix wells when used as control for environmental monitoring contains environmental swabs or other sample, PanB detection mix and master mix. (When PanB is used as a sample integrity control (internal positive control) for fecal samples: the test sample, PanB detection mix, and master mix.).

Each of these assay vessels are subjected to universal PCR thermocycling, optionally, at the same time and in the same PCR thermocycler apparatus or separately. Universal PCR thermocycling is thermocycling that will amplify every target polynucleotide and control regardless of the make-up of the polynucleotide or if the target or control polynucleotides are RNA or DNA. One example of universal PCR thermocycling conditions are about 40-65° C. for about 10-30 minutes; then about 45 cycles of about 94-95° C. for about 5-15 seconds, and about 60° C. for about 20-45 seconds. The probes are detected during or after the thermocycling. In one embodiment of the invention, the reactions numbered 1-3 above are all completed individually or together on one multiwell device at the same time and in the same PCR thermocycler apparatus. Reactions 4-6 above are optionally added individually or together on the one multiwell device with reactions 1-3 above, or they may be run on a separate multiwell device and/or in separate thermocycler run.

Therefore, the invention provides methods for performing a polymerase chain reaction. The methods comprising loading one or more vessels certain combinations of test reagents to determine if a test polynucleotide is present in a test sample and certain combinations of control reagents to ensure that the assay proceeds correctly and with no contamination. The vessels can be any type of suitable tube or well. In one embodiment a vessel is a well, microwell, or nanowell in a microtiter plate or multiwell device with a plurality of wells. The wells can be used to assay one or more test samples at one or more dilutions for the presence of one or more test polynucleotides. A single vessel can comprise a test sample and reagents to assay for the presence of one test polynucleotides or can comprise a test sample and reagents to assay for the presence of 2, 3, 4, 5, 10, 20 or more different test polynucleotides. The wells can be used for a variety of control reactions. In one embodiment of the invention a single microtiter well plate or multiwell device contains a variety of testing and control wells. The wells on a signal plate can be two or more testing wells for the presence of DNA test polynucleotides and RNA test polynucleotides.

In one embodiment of the invention one or more vessels (e.g. one or more wells of a microtiter plate or multiwell device) comprise:
(a) a test sample;
(b) an internal sample control detection mix comprising one or more forward primers, one or more reverse primers, and one or more probes that can amplify and detect one or more conserved eukaryotic polynucleotides, such as eukaryotic 18S DNA;
(c) an assay specific target polynucleotide detection mix for a DNA target polynucleotide, assay specific target polynucleotide detection mix for a RNA target polynucleotide; or detection mix for a DNA and a RNA target polynucleotide;
(d) internal positive control detection mix; and
(e) master mix comprising one or more polymerases, nucleoside triphosphates, and optionally one or more reverse transcriptases;

The vessels are all subjected to universal polymerase chain reaction thermocycling conditions at the same time in the same thermocycler.

Additional vessels can comprise:
(a) pooled target positive control polynucleotides or a single target positive control polynucleotide;
(b) a signature sequence;
(c) a detection mix for a DNA target polynucleotide, detection mix for a RNA target polynucleotide; or detection mix for a DNA and a RNA target polynucleotide; and
(d) master mix comprising one or more polymerases, nucleoside triphosphates, and optionally one or more reverse transcriptases.

Additional vessels can comprise:
(a) water or buffer;
(b) a detection mix for a DNA target polynucleotide, detection mix for a RNA target polynucleotide; or detection mix for a DNA and a RNA target polynucleotide; and (c) master mix comprising one or more polymerases, nucleoside triphosphates, and optionally one or more reverse transcriptases.

Additional optional vessels can comprise:
(a) a test sample;
(b) a DNA internal positive control (IPC) polynucleotide, an RNA internal positive control polynucleotide (IPC), or both a DNA and an RNA positive control polynucleotide, wherein the DNA IPC and the RNA IPC share one or two same or similar forward primer binding regions, probe binding regions, or reverse primer binding regions and wherein one or two of the forward primer binding regions, probe binding regions, or reverse primer binding regions are different;
(c) internal positive control detection mix; and
(d) master mix comprising one or more polymerases, nucleoside triphosphates, and optionally one or more reverse transcriptases.

Additional optional vessels can comprise:
(a) a sample to be tested for contamination (e.g., a reagent or reagent mix of suspected of being contaminated);
(b) detection mix for a signature sequence; and
(c) master mix comprising one or more polymerases, nucleoside triphosphates, and optionally one or more reverse transcriptases.

Additional optional vessels can comprise:
(a) a sample to be tested for contamination or a test sample;
(b) PanB detection mix comprising one or more forward primers, one or more reverse primers, and one or more probes that can amplify and detect one or more conserved prokaryotic polynucleotides, such as 16S rDNA; and
(c) master mix comprising one or more polymerases, nucleoside triphosphates, and optionally one or more reverse transcriptases.

One embodiment of the invention provides a method for performing a polymerase chain reaction that amplifies both a DNA target polynucleotide and an RNA target polynucleotide on the same multiwell device comprising loading two or more vessels on the same multiwell device with:
(a) a test sample;
(b) an internal sample control detection mix comprising one or more forward primers, one or more reverse primers, and one or more probes that can amplify and detect one or more conserved eukaryotic polynucleotides;
(c) an assay specific target polynucleotide detection mix for a DNA target polynucleotide comprising one or more assay specific forward primers, one or more assay specific reverse primers, and one or more assay specific probes and an assay specific target polynucleotide detection mix for a RNA target polynucleotide comprising one or more assay specific forward primers, one or more assay specific reverse primers, and one or more assay specific probes; or a combined detection mix for DNA and RNA target polynucleotides; and
(d) master mix comprising one or more DNA polymerases, nucleoside triphosphates, and one or more reverse transcriptases.

The multiwell device is subjected to universal polymerase chain reaction thermocycling conditions at the same time in the same thermocycler.

One well can contain, for example, a test sample; an internal sample control detection mix comprising one or more forward primers, one or more reverse primers, and one or more probes that can amplify and detect one or more conserved eukaryotic polynucleotides; an assay specific target polynucleotide detection mix for a DNA target polynucleotide comprising one or more assay specific forward primers, one or more assay specific reverse primers, and master mix comprising one or more DNA polymerases and nucleoside triphosphates. A second well on the same multiwell device can contain, for example, a test sample; an internal sample control detection mix comprising one or more forward primers, one or more reverse primers, and one or more probes that can amplify and detect one or more conserved eukaryotic polynucleotides; one or more assay specific probes and an assay specific target polynucleotide detection mix for a RNA target polynucleotide comprising one or more assay specific forward primers, one or more assay specific reverse primers, and one or more assay specific probes; and master mix comprising one or more reverse transcriptases.

Alternatively, one well can contain a test sample; an internal sample control detection mix comprising one or more forward primers, one or more reverse primers, and one or more probes that can amplify and detect one or more conserved eukaryotic polynucleotides; an assay specific target polynucleotide detection mix for a DNA target polynucleotide comprising one or more assay specific forward primers, one or more assay specific reverse primers, and one or more assay specific probes and an assay specific target polynucleotide detection mix for a RNA target polynucleotide comprising one or more assay specific forward primers, one or more assay specific reverse primers, and one or more assay specific probes; and master mix comprising one or more DNA polymerases, nucleoside triphosphates, and one or more reverse transcriptases.

Additional wells containing reagents as discussed above can also be loaded on the same multiwell device. The universal polymerase chain reaction thermocycling conditions can be, e.g., 40-60° C. for 10-30 minutes; then about 45 cycles of 94-95° C. for 5-10 seconds, and 60° C. for 20-30 seconds.

Kits

Kits of the invention are advantageous because they contain several universal components that can be used with one or more assay specific components. See FIG. 3A-B. In one example, the detection mix is assay specific. That is, the assay specific target polynucleotide detection mix comprises one or more primers (forward and reverse) and one or more probes for the detection of 1, 2, 3, 4, 5, 6, 7, 8, 9, 10, 20, 30, 40, 50, 60, 70, 80, 90, 100, 150, 200 or more specific nucleic acid molecules. The detection mix can optionally also contain detection mix for an ISC.

The assay-specific detection mix component is combined with the universal components. The universal components include (1) RNA master mix, DNA master mix, or a combination of DNA master mix and RNA master mix (in separate containers or combined into one master mix); (2) a target positive control with signature sequence (target positive control may be pooled or single control) and detection mix for target positive control and signature sequence; and (3) detection mix for an ISC (which can be combined with target positive control detection mix). Optionally, one or more quality control detection mixes can be added to the universal components.

Therefore, the end user can purchase a universal component kit and then buy the assay-specific detection components (e.g., detection mixes) as needed. In one embodiment of the invention, one or more specific detection mixes are packaged with the universal components.

All patents, patent applications, and other scientific or technical writings referred to anywhere herein are incorporated by reference herein in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The term "about" when used with a numerical value means that the numerical value can vary by 5%. For example, "about 100" means 95 to 105.

The following are provided for exemplification purposes only and are not intended to limit the scope of the invention described in broad terms above.

EXAMPLES

Example 1 Bluetongue Virus, *Mycobacterium avium* ss. *Paratuberculosis*, and Ovine Viral Diarrhea Virus Reaction Preparation: Reaction mixes were prepared in a class 100 clean room, and contain equal parts DNA master mix and target specific detection mix for a total volume of 5 μL×number of samples to be tested. Reaction mixes were pipetted into a 96-well microtiter plate and transported to a separate work space for the addition of sample. Samples consisted of either synthetic oligonucleotides or nucleic acid purified from clinical samples (see below). Sample (5 μL) was added to appropriate wells, the plate was covered with an optical plate cover and placed into a Life Technologies ViiA™7 or a Roche LightCycler® 480. Upon completion of the cycling program, the instrument software was used to calculate the threshold value for each target and determine the sample crossing points (Cp). For analytical sensitivity testing synthetic oligonucleotides matching the target sequence were resuspended and diluted in storage buffer. For analytical specificity testing standard nucleotide BLAST searches were performed using each test target sequence as the query. Orthologs were identified and either genomic DNA was prepared from the identified organism, or synthetic DNA oligonucleotides matching the orthologous sequence were ordered as described above.

Clinical samples were purified using a commercial total nucleic acid extraction kit. Samples were spiked with synthetic DNA or RNA IPC prior to extraction. True sample status was confirmed either by ELISA or DNA sequencing.

The BTV (Bluetongue virus) PCR assay has the ability to detect at least 8 serotypes of the Bluetongue virus (Table 1). The target consisted of $10^4$ copies per reaction of synthetic DNA completely matching the subtype sequence.

TABLE 1

Bluetongue Virus Specificity Testing

| | Synthetic Positive Controls | | | | | | | |
|---|---|---|---|---|---|---|---|---|
| | BTV 1 | BTV 2 | BTV 3 | BTV 4 | BTV 5 | BTV 6 | BTV 7 | BTV 8 |
| Value 1 | 22.9 | 24.81 | 23.52 | 24.39 | 24.24 | 25.76 | 24.8 | 24.72 |
| Value 2 | 22.84 | 24.81 | 23.63 | 24.34 | 24.63 | 25.31 | 24.74 | 25.07 |
| Value 3 | 22.7 | 24.85 | 23.73 | 24.61 | 24.38 | 25.76 | 24.85 | 24.89 |
| Avg | 22.81 | 24.82 | 23.63 | 24.45 | 24.42 | 25.61 | 24.80 | 24.89 |
| Stdv | 0.10 | 0.02 | 0.11 | 0.14 | 0.20 | 0.26 | 0.06 | 0.18 |

Standard and amplification curves for Bluetongue virus showed that the detection of serotype 1 target DNA remained linear over a 108-fold change in starting target concentration. The efficiency for the reaction was 103.2% as calculated by the instrument software. A series of 1:10 dilutions of synthetic DNA representing the BTV target resulted in satisfactory amplification curves for serotype 1 BTV. The test was able to accurately detect a minimum of 10 copies per reaction. A synthetic RNA IPC was spiked into bovine whole blood samples and was detectable in total nucleic acid preparation.

For *Mycobacterium avium* ss. *paratuberculosis* the assay was shown to detect one copy of synthetic DNA representing the target sequence. The reverse transcription cycling step did not adversely affect results.

For Bovine Viral Diarrhea Virus, 15 confirmed BVDV-positive samples were tested using the assay reagents. Serum samples were purified for total nucleic acid and tested following the RealPCR protocol. The protocol is 40-60° C. for 10-30 minutes; then 45 cycles of 94-95° C. for 5-10 seconds, and 60° C. for 20-30 seconds.

The sample pool consisted of 5 different BVDV types. All 15 samples returned sigmoid shaped amplification curves and were called positive by the instrument software.

These results confirm the specificity and sensitivity of RealPCR diagnostic real-time PCR platform. The assays have a minimal sensitivity of 10 copies of target nucleic acid per 5 μL sample. The results demonstrate the ability to use a single cycling protocol to run either DNA or RNA targets, greatly simplifying the user experience.

Example 2

This example demonstrates the feasibility of using a combined RNA/DNA internal positive control (IPC) for use in real time PCR (qPCR). In qPCR tests, the IPC is used to determine i) the effective nucleic extraction from a given sample and ii) the successful amplification and detection of a specific segment of DNA (target).

Both RNA and DNA IPC single stranded oligonucleotides were synthesized according to the sequences in FIG. 1A by Integrated DNA Technologies (Coralville, Iowa). Lyophilized Ultramer™ oligonucleotides were resuspended and diluted in RNA-safe buffer (RSB) containing 10 mM Tris, pH 7.0, 0.05% sodium azide, 0.05% Tween® (polysorbate) 20, 0.1 mM EDTA, and 50 ng/uL poly-A RNA. Dilutions of the ultramers were stored at −20° C. until needed.

A hydrolysis probe based testing format was used to detect the presence of DNA. For internal positive controls, the DNA and RNA oligonucleotides were designed to share sequences corresponding to the reverse primer and the hydrolysis (TaqMan®) probe binding sites. However, the DNA and RNA IPCs differed in the forward primer binding site, as shown in FIG. 1A, 1B. For the detection of either RNA or DNA IPC, the shared probe, the shared reverse primer and the specific forward primer were mixed to create either the RNA or DNA detection mix (FIG. 1B). Primer concentrations for IPC detection mixes were 100 nM while the probes were at 80 nM. For *mycoplasma* testing, *Mycoplasma gallisepticum* primers and probes were based on a previously published test for this organism as shown in Table 1 (Raviv & Kleven, Avian Diseases, 53:103 (2009)). The length of the primers was increased and the locations adjusted slightly to allow for annealing at 60° C. To allow for multiplexing, the *mycoplasma* probe contained a FAM-TAMRA fluorophore-quencher combination while the IPC used a HEX-TAMRA combination. All reactions were performed in a Life Technologies ViiA 7 real-time PCR machine using a thermocycling program of: 60° C. for 5 min., 65° C. for 5 min., 95° C. for 30 sec.; 45 cycles of: 95° C. for 5 sec., 60° C. for 20 sec.; 40° C. hold. Fluorescent readings were taken in both the FAM and HEX channels. Real-time PCR reactions were run with AptaTaq® Genotyping Master from Roche. AptaTaq is a hot-start DNA polymerase containing 5' to 3' exonuclease activity.

This experiment demonstrates the ability of a given detection mix to detect the presence of either a DNA IPC or an RNA IPC, when the DNA IPC and the IPC RNA IPC contain identical forward primer and probe binding sites, but differ in reverse primer binding sites. Avian tracheal swabs were soaked in 200 microliters of PBS and used as a sample for the extraction of total nucleic acid using a Quiagen QIAamp DNA Mini Kit (Qiagen product code 51304).

Immediately prior to sample lysis, the lysis buffer was spiked with either a mixture of RNA and DNA IPC, RNA IPC alone, or DNA IPC alone. Total nucleic acid was then purified from each resulting spiked sample, and tested with *M. gallisepticum* detection mix and either RNA IPC detection mix or DNA IPC detection mix in a multiplex real-time PCR reaction (Table 2). The tests were done in triplicate. When the reaction contained *mycoplasma* specific detection mix as well as RNA IPC detection mix, *mycoplasma* DNA was detected in all samples as expected. However, the RNA IPC detection mix was unable to detect the presence of either the RNA IPC or the DNA IPC. This indicates that the RNA IPC detection mix does not allow for the amplification of the DNA IPC. The lack of amplification of the RNA IPC with the RNA IPC detection mix was due to the AptaTaq master mix lacking reverse transcriptase activity and thus being unable to generate cDNA from RNA. Thus, the sequence variation between the DNA and RNA IPCs is sufficient to prevent amplification of DNA IPC with the RNA IPC detection mix.

TABLE 2

Outline of experimental design for a DNA target detection mix. Results are indicated with "+" or "−" to indicate detection of target or spiked IPC. Mycoplasma DNA was in every sample and therefore expected to be detected in all wells.

| DNA Target | Target | Spiked IPC oligo | | |
|---|---|---|---|---|
| Detection mix | MG | DNA/RNA | RNA | DNA |
| *M. gallisepticum* DMx & RNA IPC DMx | + | − | − | − |
| *M. gallisepticum* DMx & DNA IPC DMx | + | + | − | + |

When the multiplex reactions contained *mycoplasma* detection mix as well as DNA IPC detection mix, again all test reactions indicated the presence of *mycoplasma* as expected. Conversely, no RNA IPC was detected, demonstrating the lack of specificity of the DNA detection mix for the RNA IPC. However, when either the RNA/DNA IPC mix or DNA IPC alone was spiked into the sample, the DNA IPC detection mix was able to amplify and signal the presence of the DNA IPC. Together, these results show the ability to selectively amplify and detect either the DNA IPC or the RNA IPC from a mixture containing both a DNA IPC and an RNA IPC.

TABLE 3

Outline of experimental design for a RNA target detection mix. Results are indicated with "+" or "−" to indicate detection of target or spiked IPC. BVDV RNA was in every sample and therefore expected to be detected in all wells.

| RNA Target | Target | Spiked IPC oligo | | |
|---|---|---|---|---|
| Detection mix | BVDV | DNA/RNA | RNA | DNA |
| BVDV DMx & RNA IPC DMx | + | + | + | − |
| BVDV DMx & DNA IPC DMx | + | + | − | + |

The mixed RNA/DNA IPC was also applied using a test for an RNA target. For this, a bovine whole blood sample was taken from a known Bovine Viral Diarrhea Virus (BVDV) positive animal. Total RNA from the sample was purified using a QIAamp Viral RNA kit (Qiagen, #52904). This sample was spiked with either a mixture of RNA and DNA IPC, RNA IPC alone, or DNA IPC alone. Each resulting spiked sample was then tested with BVDV detection mix and either RNA IPC detection mix or DNA IPC detection mix in a multiplex real-time PCR reaction (Table 3). The tests were done in triplicate. In all cases, the BVDV detection mix was able to amplify and signal the presence of BVDV RNA. When the RNA IPC detection mix was added, signals were detected from the IPC probe only when RNA IPC was the spiked material (both the conditions containing mixed RNA/DNA IPC and RNA IPC alone). No signal was detected when the sample was only spiked with DNA IPC. This indicates the RNA IPC detection mix is specific for the RNA IPC, and does not amplify and/or signal the presence of the DNA IPC. Alternatively, when the multiplex reactions contained the DNA IPC DMx, only conditions which contained the DNA IPC spike produced a signal from the IPC probe. No signal was generated when using the DNA IPC detection mix and an RNA IPC spike. This indicates that the DNA IPC detection mix is specific for the DNA IPC.

In total, these results show that the presence of either RNA or DNA IPC can be selectively detected, depending on the detection mix used, and that neither the RNA nor the DNA detection mix will cross-react with the opposite IPC. Moreover, the RNA IPC added to a DNA test does not interfere with the detection of target DNA or the DNA IPC. Additionally, the DNA IPC added to an RNA test does not interfere with the detection of the target RNA or the RNA IPC.

These examples show the feasibility of using a combination of synthetic RNA and DNA IPCs for use as controls in real-time PCR reactions, using a hydrolysis probe based real-time PCR system and uniquely designed synthetic IPC polynucleotides, which share probe and reverse primer sequences but differ in forward primer sequence. In this system, it is possible to selectively amplify and signal the presence of the DNA IPC.

Example 3: Internal Positive Control

Three pairs of synthetic DNA and RNA IPCs (DNA-A and RNA-A; DNA-B and RNA-B; DNA-C and RNA-C; FIG. 2) were manufactured with randomized combinations for the forward, probe and reverse region sequences. Corresponding detection mixes (DMx-A through F) were also generated for detection of each DNA or RNA IPC. DMx-A is designed for amplification and detection of DNA-A, DMx-B is designed for amplification and detection of RNA-A, DMx-C is designed for amplification and detection of DNA-B, DMx-D is designed for amplification and detection of RNA-B, DMx-E is designed for amplification and detection of DNA-C and DMx-F is designed for amplification and detection of RNA-C.

Each of the three DNA IPCs was tested with each of the six detection mixes (Table 4). The DNA constructs were only detected by the detection mix that was designed to amplify the respective synthetic sequence (Table 4A). For the RNA IPCs only the RNA detection mixes were evaluated. Two of the three detection mix/IPC pairings tested positive. IPC RNA-B unexpectedly tested negative with DMx-E; however, it was noted by the vendor that there were manufacturing issues with RNA-B and this may be the reason for the negative result (Table 4B).

The thermocycling parameters used for both RNA IPCs and DNA IPCs was: 60° C. for 5 min., 65° C. for 5 min., 95° C. for 30 sec.; 45 cycles of: 95° C. for 5 sec., 60° C. for 20 sec.; 40° C. hold. This demonstrates that a single thermocycling protocol will support both PCR and RT-PCR reactions.

These results show that the presence of each of the IPCs can be detected by its corresponding detection mix. Although some of the DNA and RNA IPCs have shared probe and/or primer binding sites, each IPC will only be detected by its corresponding detection mix. The detection mixes do not cross-amplify and/or detect IPCs for whose amplification they were not designed.

TABLE 4A

| DMx design | DNA IPC | | |
| --- | --- | --- | --- |
|  | DNA-A | DNA-B | DNA-C |
| DMx-A | + | − | − |
| DMx-B | − | − | − |
| DMx-C | − | − | + |
| DMx-D | − | − | − |

TABLE 4A-continued

| DMx design | DNA IPC | | |
| --- | --- | --- | --- |
|  | DNA-A | DNA-B | DNA-C |
| DMx-E | − | − | − |
| DMx-F | − | − | − |

TABLE 4B

| DMx design | RNA IPC | | |
| --- | --- | --- | --- |
|  | RNA-A | RNA-B | RNA-C |
| DMx-D | + | − | − |
| DMx-E | − | − | − |
| DMx-F | − | − | + |

Example 4: Pooled Positive Control (PPC) and Signature Sequence

A pooled target positive control was prepared that was composed of 11 DNA positive control targets (see Table 5) and the signature sequence. The test targets were each at 1000 copies/reaction while the signature was added at 4000 copies/reaction. The solution was tested with individual detection mixes for each target.

The thermocycling parameters were: 60° C. for 5 min., 65° C. for 5 min., 95° C. for 30 sec.; 45 cycles of: 95° C. for 5 sec., 60° C. for 20 sec.; 40° C. hold.

This experiment demonstrates that each control in the pool is amplifiable at a similar sensitivity and that the controls do not interfere with each other. The signature sequence is detectable at a lower cycle number than the pooled target positive controls, as expected due to the higher copy number of input template.

TABLE 5

| Target/Detection Mix | Cp Value |
| --- | --- |
| *M. gallisepticum* (MG) | 28.75 |
| *M. synoviae* (MS) | 28.9 |
| *M. meleagridis* | 29.14 |
| *Mycobacterium paratuberculosis* (MAP) | 29.52 |
| *Mycoplasma bovis* | 29.65 |
| *Leptospira* spp | 28.7 |
| *Clostridium perfringens*- Enterotoxin A | 29.23 |
| *Clostridium perfringens* | 28.92 |
| *Lawsonia* | 28.35 |
| Influenza A | 29.02 |
| Coxiella B | 28.32 |
| Signature | 25.73 |

Example 5: PPC and Signature Dilution Series

Contamination of PCR reactions with PPC can result in false positive results. The detection of any such contamination event is therefore desirable. In order to simulate the detectability of a contamination with PPC containing a signature sequence, the pool described in Example 4 above was serially diluted 1:2 to a dilution of 1:2048. Each dilution was tested for three of the disease specific controls represented in the pool, as well as for the signature sequence.

The thermocycling parameters were: 60° C. for 5 min., 65° C. for 5 min., 95° C. for 30 sec.; 45 cycles of: 95° C. for 15 sec., 60° C. for 30 sec.; 40° C. hold.

While the signature sequence was detectable out to a dilution of 1:512, each of the three disease specific controls was detectable out to 1:64 or 1:128. This corresponds well with the four-fold copy number of signature sequence as compared to each control in the pool. Thus, the design of the pool ensures that the detection of any contamination event is detectable with high sensitivity and robustness. The results demonstrate that the signature can be used as a sensitive tracer to detect a contamination with PPC.

TABLE 6

| Dilution | MAP | MG | MS | Signature |
|---|---|---|---|---|
| | | Cp Average | | |
| PPC | 27.6 | 27.6 | 27.0 | 24.8 |
| 1:2 | 28.9 | 28.5 | 27.5 | 25.6 |
| 1:4 | 30.1 | 29.2 | 27.7 | 26.5 |
| 1:8 | 31.1 | 29.7 | 27.9 | 27.2 |
| 1:16 | 32.1 | 30.2 | 28.8 | 28.1 |
| 1:32 | 32.5 | 30.5 | 28.5 | 28.6 |
| 1:64 | 34.9 | 31.7 | 29.1 | 29.2 |
| 1:128 | 34.3 | 32.0 | — | 29.4 |
| 1:256 | — | — | — | 30.0 |
| 1:512 | — | — | — | 31.0 |
| 1:1024 | — | — | — | — |
| 1:2048 | — | — | — | — |

Example 6: Minimer Design

FIG. 5A depicts a hypothetical example of a real time RT-PCR design that targets the hydroxymethylbilane synthase (hmbs1) gene of *Bos taurus*. The forward and reverse primer binding sites are single underlined, while the positive strand probe is double underlined. The reverse primer spans an exon-exon junction, and therefore this amplicon would be predicted to amplify mRNA selectively. The naturally occurring amplicon measures 166 bases in length and therefore cannot readily be synthesized as an RNA oligomer. FIG. 5B depicts a minimer version of the hmbs1 design, in which the sequences intervening the primer and probe binding sites are greatly shortened, resulting in an amplicon of 61 bases. With the addition of eight bases at the 5' end and nine bases at the 3' end, the total length of 78 bases is expected to be readily synthesized by current commercial techniques, allowing the production of a synthetic RNA molecule that can serve as a target positive control for HMBS1 in a real time RT-PCR test (for example as an endogenous host target (ISC)).

Example 7: Minimer Amplification

A real time RT-PCR diagnostic test was designed to amplify and detect the presence of BVDV genomic RNA. The naturally occurring target amplicon is 206 bases in length. To create a positive control for this test, a minimer RNA amplicon was designed and synthesized as a control for the proper activity of the primer and probe detection reagents. The resulting minimer amplicon is 65 bases in length. For comparison, a synthetic DNA molecule of 236 bases was used as a template for the same test.

The minimer RNA template and the synthetic DNA template were PCR amplified in a single run of a thermocycler, and on the same microtiter plate. The thermocycling parameters were: 60° C. for 5 min., 65° C. for 5 min., 95° C. for 30 sec.; 45 cycles of: 95° C. for 15 sec., 60° C. for 30 sec.; 40° C. hold. The PCR reactions of the DNA and the RNA template were assembled from the same master mix, which contained HawkZO5, an enzyme that incorporates both DNA-dependent and RNA-dependent (i.e. reverse transcriptase) DNA polymerase activities (Roche Diagnostics Corporation, Indianapolis, Ind., U.S.A.).

As shown in FIG. 6A, the synthetic minimer RNA amplicon was an effective template for reverse transcription and subsequent DNA amplification. As shown in FIG. 6B, the DNA template produced similar results as the RNA template. These results demonstrate the feasibility and utility of synthetic RNA minimers as positive controls in PCR tests.

Surprisingly, the DNA template amplified efficiently, despite the fact that both the detection mix and the cycling program were originally designed for RNA amplification, i.e., the detection mix contained HawkZO5 reverse transcriptase and the thermocycling program included steps designed to support the reverse transcription of RNA into DNA.

Therefore, through the methods of the invention, both RNA and DNA polynucleotides can be amplified using a single master mix using an enzyme having DNA-dependent polymerase activity and RNA-dependent DNA polymerase activities (e.g., HawkZO5). In addition, both RNA and DNA polynucleotides can be amplified with a single thermocycling program. Therefore, both RNA and DNA polynucleotides can be amplified simultaneously in a single thermocycler. Both RNA and DNA polynucleotides can be amplified in same or separate reaction vessels located on a single multiwell device, such as a microtiter plate, or a device having a multitude of microwells or nanowells.

Example 8: Universality of Components

Synthetic control oligonucleotides were manufactured for the targets listed in Table 7. (*M. synoviae, M. gallisepticum*, avian GADPH, BVDV, and the signature sequence). A pooled target positive control was prepared that was composed of each synthetic oligonucleotide. All oligonucleotides were used at 1000 copies/reaction except for the signature sequence, which was added at 4000 copies/reaction. The solution was tested in triplicate with the respective detection mixes for each target. The MG/MS detection mix is a multiplex for MG, MS and GAPDH. The BVDV and signature sequence tests are monoplex. The BVDV oligonucleotide was an RNA minimer version of a naturally occurring target RNA sequence, as shown in Example 7. All reactions were carried out in a single instrument run on the same plate and thus using the same thermocycling program.

The thermocycling parameters were: 60° C. for 5 min., 65° C. for 5 min., 95° C. for 30 sec.; 45 cycles of: 95° C. for 15 sec., 60° C. for 30 sec.; 40° C. hold.

All five targets were successfully amplified from the pool. This experiment demonstrates that a PPC can comprise both RNA and DNA nucleic acids; that both PCR and RT-PCR reactions can be carried out with a single thermocycling protocol; that both PCR and RT-PCR reactions can be carried out on a single plate and/or in a single instrument run; that detection of an ISC can be multiplexed with the detection of at least one disease target in the same reaction vessel (well); and that a minimer can be employed as a positive control for a longer, naturally occurring target sequence.

TABLE 7

| Detection Mix | Master Mix | Target | Cp value |
|---|---|---|---|
| MG/MS DMx | DNA | *M. synoviae* (MS) | 27.45 |
| | | *M. gallisepticum* (MG) | 27.53 |
| | | GAPDH (ISC) | 26.38 |
| BVDV | RNA | BVDV | 26.84 |
| Signature | DNA | Signature | 25.77 |

We claim:

1. A method for performing a polymerase chain reaction comprising loading a plurality of vessels as follows:
   (a) in at least one vessel (i) a test sample; (ii) an internal sample control detection mix comprising one or more forward primers, one or more reverse primers, and one or more probes that can amplify and detect one or more conserved eukaryotic polynucleotides; (iii) an assay specific target polynucleotide detection mix for a DNA target polynucleotide comprising one or more assay specific forward primers, one or more assay specific reverse primers, and one or more assay specific probes; or an assay specific target polynucleotide detection mix for a RNA target polynucleotide comprising one or more assay specific forward primers, one or more assay specific reverse primers, and one or more assay specific probes; or a combined detection mix for DNA and RNA target polynucleotides; and (iv) master mix comprising one or more DNA polymerases, nucleoside triphosphates, and optionally one or more reverse transcriptases;
   (b) in at least one vessel (i) an assay specific target polynucleotide detection mix for a DNA target polynucleotide comprising one or more assay specific forward primers, one or more assay specific reverse primers, and one or more assay specific probes; or an assay specific target polynucleotide detection mix for a RNA target polynucleotide comprising one or more assay specific forward primers, one or more assay specific reverse primers, and one or more assay specific probes; or a combined detection mix for DNA and RNA target polynucleotides; and (ii) master mix comprising one or more DNA polymerases, nucleoside triphosphates, and optionally one or more reverse transcriptases; and
   (c) in at least one vessel (i) a pooled target positive control polynucleotide mix comprising a plurality of control polynucleotides including a control polynucleotide for a target, which control polynucleotide is detectable by the assay specific target polynucleotide detection mix in step (c)(ii);
   wherein the pooled target positive control polynucleotide mix comprises a signature sequence polynucleotide; (ii) an assay specific target polynucleotide detection mix for a DNA target polynucleotide comprising one or more assay specific forward primers, one or more assay specific reverse primers, and one or more assay specific probes; or an assay specific target polynucleotide detection mix for a RNA target polynucleotide comprising one or more assay specific forward primers, one or more assay specific reverse primers, and one or more assay specific probes; or a combined detection mix for DNA and RNA target polynucleotides; and (iii) master mix comprising one or more DNA polymerases, nucleoside triphosphates, and optionally one or more reverse transcriptases;
   and subjecting the plurality of vessels to the same polymerase chain reaction thermocycling conditions at the same time in the same thermocycler.

2. The method of claim 1, wherein at least one of the plurality of vessels is loaded with both an assay specific target polynucleotide detection mix for a DNA target polynucleotide and with an assay specific target polynucleotide detection mix for a RNA target polynucleotide.

3. The method of claim 1, further comprising:
(i) additionally loading the vessel of claim 1 (a) with a combination of:
   (a) a DNA internal positive control (IPC), an RNA internal positive control (IPC), or both a DNA and an RNA internal positive control, wherein the DNA IPC and the RNA IPC share one or two same or similar forward primer binding regions, probe binding regions, or reverse primer binding regions, and wherein one or two of the forward primer binding regions, probe binding regions, or reverse primer binding regions of the DNA IPC are different from the one or two of the forward primer binding regions, probe binding regions, or reverse primer binding regions of the RNA IPC; and
   (b) internal positive control detection mix comprising one or more internal positive control forward primers, one or more internal positive control reverse primers, and one or more internal positive control probes; or
(ii) loading at least one additional vessel with a combination of:
   (a) a test sample;
   (b) a DNA internal positive control (IPC), an RNA internal positive control (IPC), or both a DNA and an RNA internal positive control, wherein the DNA IPC and the RNA IPC share one or two same or similar forward primer binding regions, probe binding regions, or reverse primer binding regions, and wherein one or two of the forward primer binding regions, probe binding regions, or reverse primer binding regions of the DNA IPC are different from the one or two of the forward primer binding regions, probe binding regions, or reverse primer binding regions of the RNA IPC;
   (c) internal positive control detection mix comprising one or more internal positive control forward primers, one or more internal positive control reverse primers, and one or more internal positive control probes; and
   (d) master mix comprising one or more DNA polymerases, nucleoside triphosphates, and optionally one or more reverse transcriptases.

4. The method of claim 3, wherein the DNA internal positive control, RNA internal positive control, or both the DNA internal positive control and RNA internal positive control are universal components that can be used with any assay specific target polynucleotide detection mix.

5. The method of claim 1 wherein one or more of the target positive control polynucleotides comprises a forward primer binding region, a probe binding region, and a reverse primer binding region, wherein each of the forward primer binding region, the probe binding region, and the reverse primer binding region have homology to a corresponding forward primer binding region, a probe binding region and a reverse primer binding region in a target polynucleotide, and wherein one or more of the pooled target positive control polynucleotides have 10 or more fewer nucleic acid bases than a region of the target polynucleotide comprising the forward primer binding region, the probe binding region, the reverse primer binding region and any intervening regions for which the one or more target positive control polynucleotides serve as a control.

6. The method of claim 1, further comprising:
(i) loading at least one additional vessel with a combination of:
   (a) a sample to be tested for contamination;
   (b) detection mix for a signature sequence; and
   (c) master mix comprising one or more DNA polymerases, nucleoside triphosphates, and optionally one or more reverse transcriptases; or
(ii) additionally loading the vessel of claim 1 (a) with:
   (a) detection mix for a signature sequence.

7. The method of claim 1, further comprising:
(i) loading at least one additional vessel with a combination of:
   (a) optionally, a sample to be tested for contamination or a test sample;
   (b) PanB detection mix comprising one or more forward primers, one or more reverse primers, and one or more probes that can amplify and detect one or more conserved prokaryotic polynucleotides; and
   (c) master mix comprising one or more DNA polymerases, nucleoside triphosphates, and optionally one or more reverse transcriptases; or
(ii) additionally loading the vessel of claim 1 (a) with:
   (a) PanB detection mix comprising one or more forward primers, one or more reverse primers, and one or more probes that can amplify and detect one or more conserved prokaryotic polynucleotides.

8. The method of claim 1, wherein the polymerase chain reaction is a real-time polymerase chain reaction.

9. The method of claim 1, wherein the pooled target positive control polynucleotides comprise 2, 5, 10, 20, 30 or more target positive control polynucleotides for 2, 5, 10, 20, 30 or more target polynucleotides.

10. The method of claim 9, wherein pooled target positive control polynucleotides comprise both DNA and RNA target positive control polynucleotides.

11. The method of claim 1, wherein the molar concentration of the signature sequence polynucleotide is greater than the molar concentration of one or more of the target positive control polynucleotides.

12. The method of claim 1, wherein the master mix and pooled target positive control polynucleotides are universal components that can be used with any assay specific target polynucleotide detection mix, wherein the pooled target positive control includes a control polynucleotide for the target detectable by the assay specific target polynucleotide detection mix in step (a)(iii).

13. The method of claim 1, wherein the assay specific target polynucleotide detection mix comprises assay specific reverse primers, assay specific forward primers, and one or more assay specific probes for two or more different target polynucleotides.

14. The method of claim 1, wherein the test sample comprises RNA polynucleotides and DNA polynucleotides.

15. The method of claim 1, wherein the thermocycling conditions are 40-65° C. for 10-30 minutes; then about 45 cycles of 94-95° C. for 5-15 seconds, and 60° C. for 20-45 seconds.

* * * * *